(12) United States Patent
Purse et al.

(10) Patent No.: US 12,329,828 B2
(45) Date of Patent: Jun. 17, 2025

(54) PYRIMIDINE NUCLEOSIDE COMPOUNDS FOR FLUORESCENCE IMAGING AND SPECTROSCOPY

(71) Applicant: San Diego State University Foundation, San Diego, CA (US)

(72) Inventors: Byron W. Purse, San Diego, CA (US); George Samaan, San Diego, CA (US); Mckenzie Wyllie, San Diego, CA (US); Julian Cizmic, San Diego, CA (US); Katrina Ngo, San Diego, CA (US); Susan Andersen, San Diego, CA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 945 days.

(21) Appl. No.: 17/476,852

(22) Filed: Sep. 16, 2021

(65) Prior Publication Data
US 2022/0088226 A1   Mar. 24, 2022

Related U.S. Application Data

(60) Provisional application No. 63/079,022, filed on Sep. 16, 2020.

(51) Int. Cl.
*A61K 49/00* (2006.01)
*C07D 471/04* (2006.01)
*C07F 9/6561* (2006.01)

(52) U.S. Cl.
CPC ........ *A61K 49/0021* (2013.01); *C07D 471/04* (2013.01); *C07F 9/6561* (2013.01)

(58) Field of Classification Search
CPC .. C07F 9/6561; C07D 471/04; A61K 49/0021
See application file for complete search history.

(56) References Cited

U.S. PATENT DOCUMENTS

| | | |
|---|---|---|
| 6,005,096 A | 12/1999 | Matteucci et al. |
| 6,414,127 B1 | 7/2002 | Lin et al. |
| 7,511,125 B2 | 3/2009 | Lin et al. |
| 8,507,661 B2 | 8/2013 | Manoharan et al. |
| 8,975,389 B2 | 3/2015 | Manoharan et al. |
| 9,725,479 B2 | 8/2017 | Manoharan et al. |
| 10,233,448 B2 | 3/2019 | Maier et al. |
| 2003/0158403 A1 | 8/2003 | Manoharan et al. |
| 2011/0130440 A1 | 6/2011 | Manoharan et al. |
| 2013/0130378 A1 | 5/2013 | Manoharan et al. |
| 2013/0203836 A1 | 8/2013 | Rajeev et al. |
| 2020/0262862 A1 | 8/2020 | Purse et al. |

FOREIGN PATENT DOCUMENTS

| | | | |
|---|---|---|---|
| WO | 9507918 A2 | 3/1995 | |
| WO | WO-2018089582 A1 * | 5/2018 | ............. C07H 19/24 |

OTHER PUBLICATIONS

Aitken et al.,"An Oxygen Scavenging System for Improvement of Dye Stability in Single-Molecule Fluorescence Experiments," Biophys J., 94(5):1826-1835, Mar. 2008.
Compound Summary for CID 59089368, Pubchem, Dec. 2017.
International Search Report and Written Opinion of the ISA/US IN PCT/U82017/060776 dated Mar. 5, 2018; 9pgs.
Malyshev et al., "A Semi-synthetic Organism with an Expanded Genetic Alphabet," Nature, 509(7500):385-388, May 2014.
Michalet et al., "Development of New Photon-Counting Detectors for Single-Molecule Fluorescence Microscopy," Philos Trans R Soc Lond B Biol Sci., 368(1611):1-22, Dec. 2012.
Narayanaswamy et al., "A Thiazole Coumarin (TC) Turn-On Fluorescence Probe for AT-Base Pair Detection and Multipurpose Applications in Different Biological Systems," Sci. Rep., 4(6476):1-10; Sep. 2014.
Ray et al., "Application of Kinase Bypass Strategies to Nucleoside Antivirals," Antiviral Res., 92(2):277-291, Nov. 2011.
Sharma et al., "Antisense Oligonucleotides: Modifications and Clinical Trials," MedChemComm, 10:1454-1471, Oct. 2014.
Turner et al., "Synthesis of Fluorescence Turn-On DNA Hybridization Probe using the DEAtC 2'-deoxycytidine Analogue," Curr Protoc Nucleic Acid Chem., 75(1):e59, Dec. 2018.
Rodgers et al., "Functionalized Tricyclic Cytosine Analogues Provide Nucleoside Fluorophores with Improved Photophysical Properties and a Range of Solvent Sensitivities," Chemistry, 20(7):2010-2015, Feb. 2014.

* cited by examiner

*Primary Examiner* — James W Rogers
(74) *Attorney, Agent, or Firm* — Haukaas Fortius PLLC; Michael Haukaas

(57) ABSTRACT

Fluorescent nucleobase surrogates capable of Watson-Crick hydrogen bonding are essential probes of nucleic acid structure and dynamics. Their limited brightness and short absorption and emission wavelengths have rendered them unsuitable for single-molecule detection. Herein, we synthesized a new tricyclic pyrimidine nucleoside analogue with a push-pull conjugated system. The resulting C-linked 8-(diethylamino)benzo[b][1,8] naphthyridin-2(1H)-one nucleoside (ABN), exhibits $\varepsilon_{442}=20,000$ $M^{-1}$ $cm^{-1}$ and $\Phi_{em,540}=0.39$ in water, increasing to $\Phi_{em}=0.50$-$0.53$ when base paired with adenine in duplex DNA oligonucleotides. Single-molecule fluorescence measurements of ABN using both one-photon and two-photon excitation demonstrate its excellent photostability and indicate that the nucleoside is present to >95% in a bright state with count rates of at least 15 kHz per molecule. This new fluorescent nucleobase analogue, which, in duplex DNA, is the brightest and most red-shifted known, is first to offer robust single-molecule fluorescence detection capabilities.

20 Claims, 8 Drawing Sheets
Specification includes a Sequence Listing.

DNA hairpin

SEQ ID NO: 1    ODN1

SEQ ID NO: 1  
SEQ ID NO: 16

ODN2  Y = A  
ODN3  Y = G

SEQ ID NO: 2  
SEQ ID NO: 17    ODN4

ODN5  Y = A  
ODN6  Y = G

SEQ ID NO: 3  
SEQ ID NO: 18    ODN7

ODN8  Y = A  
ODN9  Y = G

X = 8-(diethylamino)-3-((2R,4S,5R)-4-hydroxy-5-(hydroxymethyl)tetrahydrofuran-2-yl)benzo[b][1,8]naphthyridin-2(1H)-one (ABN)

PYRIMIDINE NUCLEOSIDE COMPOUNDS FOR FLUORESCENCE IMAGING AND SPECTROSCOPY

RELATED APPLICATIONS

This application claims priority under 35 U.S.C. § 119(e) to U.S. Provisional Patent Application No. 63/079,022, filed Sep. 16, 2020, which is incorporated herein by reference.

GOVERNMENT SUPPORT

This invention was made with government support under Grant Nos. 1709796 and 1800529 awarded by the National Science Foundation. The government has certain rights in the invention.

SEQUENCE LISTING

The instant application contains a Sequence Listing which has been filed electronically in ASCII format and is hereby incorporated by reference in its entirety. Said ASCII copy, created on Dec. 13, 2021, is named 512.014US1_SL2 and is 4290 bytes in size.

BACKGROUND OF THE INVENTION

Single-molecule fluorescence studies of biological molecules have a unique capacity to provide mechanistic insights into the relationships between structural dynamics and function, which are lost to averaging in ensemble measurements. Most of these studies have used extrinsic fluorophores, which can potentially interfere with the native biomolecular behavior and obscure local structural details. An ideal approach in this regard would be the use of intrinsically fluorescent biomolecules, prepared by the synthetic introduction of only minimal changes. It remains, however, a major challenge to attain adequate brightness and photostability in this approach. Fluorescent nucleobase analogues (FBAs) have been a mainstay of biophysical studies of nucleic acid structure and dynamics because they can be placed precisely in a desired sequence and are less structurally perturbing than proximally tethered fluorophores. They are available with a range of fluorescent properties and, in response to base pairing and stacking, their fluorescence may be quenched (e.g., 2-aminopurine), retained (e.g., tC and $^{th}G$) or turned on (e.g., $^{DEA}tC$) However, few nucleobase analogues have extinction coefficients >10$^4$ with $\Phi_{em}$>0.3; most are approximately an order of magnitude dimmer than conventional fluorophores such as Alexa Fluor 488 and rhodamine B. This lack of brightness has rendered them largely unsuitable for single-molecule fluorescence studies. Furthermore, with the current rapid development of spatially-resolved transcriptomics and genomics, there is clearly a future need for fluorescent analogues that can act as effective single-molecule probes. Conventional fluorophores typically exhibit superior optical properties to fluorescent nucleobase analogues, primarily because of their larger extinction coefficients—sometimes in excess of 10$^5$—but they need not be larger molecules. In structures such as rhodamine B, there is a prominent push-pull character, but the benzene carboxylic acid is twisted out of plane and does not contribute significantly to the photophysical properties. The fluorescent, tricyclic core is similar in size to many of the common fluorescent nucleotides, but the most important difference is that push-pull motifs are underrepresented in existing FBAs. The required positions of heteroatoms for the Watson-Crick face and the glycosidic bond make incorporation of this motif challenging.

Accordingly, there is lack of brightness for nucleobase analogues that has rendered them largely unsuitable for single-molecule fluorescence studies. Therefore, with the current rapid development of spatially-resolved transcriptomics and genomics there is clearly a need for fluorescent analogues that can act as effective single-molecule probes.

SUMMARY

In this work, we hypothesized that, by redesigning a fluorescent, tricyclic cytidine analogue to include a push-pull motif, a substantial enhancement of brightness could be obtained (Scheme 1). A comparison of $^{DEA}tC$ with rhodamine B shows that the electronic nature of two heteroatoms—S and the glycosidic N—differentiate $^{DEA}tC$ from a more conventional push-pull fluorophore. A structure redesigned by replacing both atoms with sp$^2$ C would impart the nucleoside analogue with a push-pull character, while maintaining the capacity for Watson-Crick hydrogen bonding and without further structural perturbation. The resulting nucleoside analogue, whose synthesis and characterization we report here, includes 8-(diethylamino)benzo[b][1,8]naphthyridin-2(1H)-one as a fluorescent nucleobase surrogate, and we name this new compound ABN. Single-molecule fluorescence measurements show that the compound exists to >95% in a bright state and can be detected using both one- and two-photon excitation.

Accordingly, this disclosure provides a compound of Formula IA:

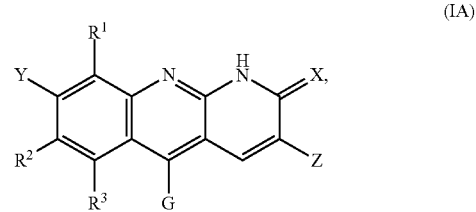

(IA)

or a salt thereof;
wherein
  X is O, S, or NR$^a$, wherein R$^a$ is H or —(C$_1$-C$_{12}$)alkyl;
  Y is NR$^b$R$^c$, OR$^d$, SR$^e$, or

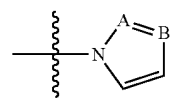

wherein A and B are each independently O, N, or S;
  G is H, halo, or —(C$_1$-C$_{12}$)alkyl;
  R$^b$, R$^c$ R$^d$, and R$^e$ are each independently H or —(C$_1$-C$_{12}$)alkyl;
  R$^3$, R$^4$, R$^5$ and R$^6$ are each independently H, halo, OH, SH, NH$_2$, or —(C$_1$-C$_{12}$)alkyl; and
  Z is a monosaccharide or peptide;
wherein each —(C$_1$-C$_{12}$)alkyl moiety is unbranched or branched, saturated or partially unsaturated, and substituted optionally with one or more halo, OH or NH$_2$.

Also, this disclosure provides a method for imaging comprising:

a) incorporating into an oligonucleotide a compound of Formula IA:

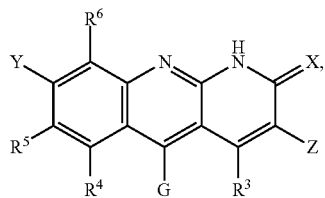

(IA)

or a salt thereof;
wherein
X is O, S, or NR$^a$, wherein R$^a$ is H or —(C$_1$-C$_{12}$)alkyl;
Y is NR$^b$R$^c$, OR$^d$, SR$^e$, or

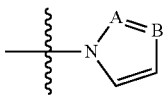

wherein A and B are each independently O, N, or S;
G is H, halo, or —(C$_1$-C$_{12}$)alkyl;
R$^b$, R$^c$ R$^d$, and R$^e$ are each independently H or —(C$_1$-C$_{12}$)alkyl;
R$^3$, R$^4$, R$^5$ and R$^6$ are each independently H, halo, OH, SH, NH$_2$, or —(C$_1$-C$_{12}$)alkyl; and
Z is a monosaccharide;
wherein each —(C$_1$-C$_{12}$)alkyl moiety is unbranched or branched, saturated or partially unsaturated, and substituted optionally with one or more halo, OH or NH$_2$;
b) exciting the base-paired compound at a suitable wavelength to form a fluorescing compound, wherein one or more photons excite a single molecule of the base-paired compound; and
c) counting the number of photons emitted by the fluorescing compound as a function of time;
wherein the base-paired compound is thereby imaged.

In some aspect of this disclosure, the method further comprises contacting a compound of Formula IA and a nucleotide or oligonucleotide under suitable conditions for oligonucleotide synthesis wherein the synthesis proceeds in the 3'- to 5'-direction and the compound is covalently bound to the nucleotide or oligonucleotide.

This technology provides novel compounds of Formulas IA, I, II and 1-5, intermediates for the synthesis of compounds of Formulas IA, I, II and 1-5, as well as methods of preparing compounds of Formulas IA, I, II and 1-5. The invention also provides compounds of Formulas IA, I, II and 1-5 that are useful as intermediates for the synthesis of other useful compounds. The invention provides for the use of compounds of Formulas IA, I, II and 1-5 for imaging of nuclei acids in vitro and in vivo.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
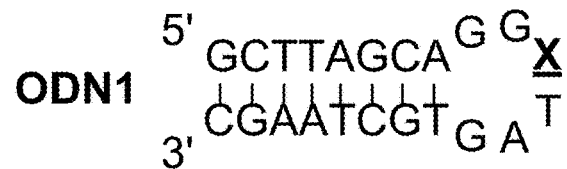
FIG. 1. Oligonucleotides used to study the fluorescence and base pairing properties of ABN.
Figure 1:
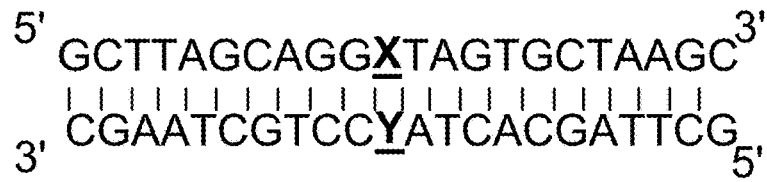
Figure 1:
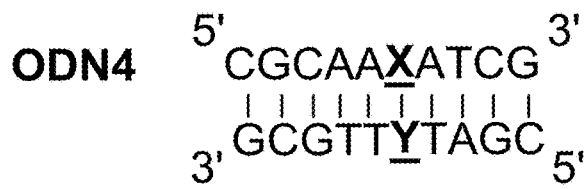
Figure 1:
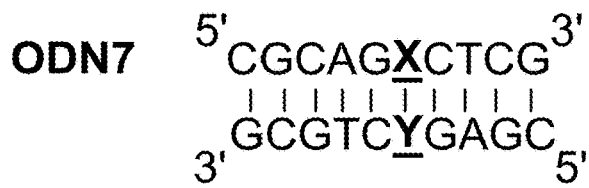

The design of this new fluorescent nucleoside analogue ABN, centered around a push-pull motif common in bright organic fluorophores, has provided an unprecedented combination of high brightness and long absorption and emission wavelengths while retaining a Watson-Crick face. Fluorescence is further enhanced when the compound is present in single-stranded and duplex oligonucleotides. ABN's robust photophysical properties and tautomeric stability allow detection of single molecules of the ABN nucleoside using either 1P or 2P at convenient excitation wavelengths for both. These results place ABN as the most promising fluorescent nucleoside analogue to date for single-molecule studies of nucleic acid structure and dynamics. A forthcoming full study will elucidate the finer details of this analogue's fluorescent properties, base pairing, tautomerism, and local structural perturbations in a variety of neighboring base sequences.

ABN tends to be photobleached with a half-life t½≈0.2 s at typical laser powers (e.g., a 488 nm continuous wavelength diode laser (iBeamSMART, Toptica, 200.46 W cm-2)). This photobleaching is a degradative reaction of the fluorophore typically caused by a reaction with oxygen when the fluorophore is in the 51 excited state. To improve photostability, oxygen scavenging systems were examined that are well established and widely used in fluorescence microscopy. The GO/CAT system is described by T J Ha: Methods in Enzymology, Volume 600, 2018, 463; Nat. Commun. 2019; 10: 5375.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2, 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

The recitation of a), b), c), . . . or i), ii), iii), or the like in a list of components or steps do not confer any particular order unless explicitly stated.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983); for heterocyclic synthesis see Hermanson, Greg T., Bioconjugate Techniques, Third Edition, Academic Press, 2013.

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below or otherwise described herein. The alkyl can also be optionally partially or fully unsaturated. As such, the recitation of an alkyl group can include an alkenyl group or an alkynyl group. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted.

The term "heteroatom" refers to any atom in the periodic table that is not carbon or hydrogen. Typically, a heteroatom is O, S, N, P. The heteroatom may also be a halogen, metal or metalloid.

The term "heterocycloalkyl" or "heterocyclyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms, wherein the ring skeleton comprises a 5-membered ring, a 6-membered ring, two 5-membered rings, two 6-membered rings, or a 5-membered ring fused to a 6-membered ring. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl.

As used herein, the term "substituted" or "substituent" is intended to indicate that one or more (for example, in various embodiments, 1-10; in other embodiments, 1-6; in some embodiments 1, 2, 3, 4, or 5; in certain embodiments, 1, 2, or 3; and in other embodiments, 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, haloalkyl, hydroxyalkyl, aryl, heteroaryl, heterocyclyl, cycloalkyl, alkanoyl, alkoxycarbonyl, amino, alkylamino, dialkylamino, carboxyalkyl, alkylthio, alkylsulfinyl, and alkyl sulfonyl.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof, such as racemic mixtures, which form part of the present invention. Many organic compounds exist in optically active forms, i.e., they have the ability to rotate the plane of plane-polarized light. In describing an optically active compound, the prefixes D and L, or R and S. are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate (defined below), which may occur where there has been no stereoselection or stereospecificity in a chemical reaction or process.

Embodiments of the Technology

This disclosure provides a compound of Formula IA:

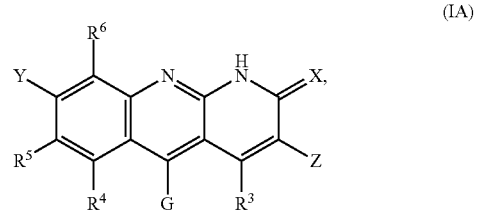

(IA)

or a salt thereof;
wherein
X is O, S, or $NR^a$, wherein $R^a$ is H or $—(C_1-C_{12})$alkyl;
Y is $NR^bR^c$, $OR^d$, $SR^e$, or

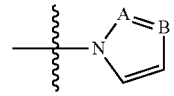

wherein A and B are each independently O, N, or S;
G is H, halo, or $—(C_1-C_{12})$alkyl;
$R^b$, $R^c$ $R^d$, and $R^e$ are each independently H or $—(C_1-C_{12})$alkyl;
$R^3$, $R^4$, $R^5$ and $R^6$ are each independently H, halo, OH, SH, $NH_2$, or $—(C_1-C_{12})$alkyl; and
Z is a monosaccharide or peptide;
wherein each $—(C_1-C_{12})$alkyl moiety is unbranched or branched, saturated or partially unsaturated, and substituted optionally with one or more halo, OH or $NH_2$.

In some embodiments, Y is $NR^bR^c$ wherein $R^b$ and $R^5$ taken together form a heterocycle with the nitrogen moiety of $NR^bR^c$ and/or $R^c$ and $R^6$ taken together form a heterocycle with the nitrogen moiety of $NR^bR^c$. In some embodiments, Y and either $R^5$ or $R^6$ taken together form a heterocycle. In some embodiments, Y and either $R^5$ or $R^6$ taken together form a N, O, or S heterocycle, wherein optionally the heterocycle is a 5-membered or 6-membered heterocycle.

Additionally, this disclosure provides a compound of Formula I:

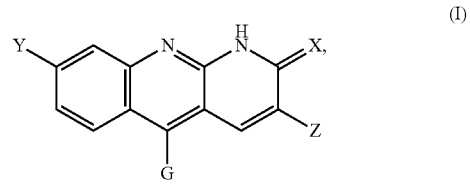

(I)

or a salt thereof;
wherein
X is O, S, $NR^a$, wherein $R^a$ is H or $—(C_1-C_{12})$alkyl;
Y is $NR^bR^c$, $OR^d$, $SR^e$;
G is H, halo, or $—(C_1-C_{12})$alkyl;
$R^b$, $R^c$ $R^d$, and $R^e$ are each independently H or $—(C_1-C_{12})$alkyl; and
Z is a monosaccharide or peptide;

wherein each —(C₁-C₁₂)alkyl is unbranched or branched, and substituted optionally with one or more halo, OH or NH$_2$.

In some embodiments, $R^a$ is H or —(C₁-C₆)alkyl; G is H, halo, or —(C₁-C₆)alkyl; $R^b$, $R^c$, $R^d$, and $R^e$ are each independently H or —(C₁-C₆)alkyl; and Z is a monosaccharide.

In some other embodiments of this disclosure, the compound is represented by the following Formulas (1-5):

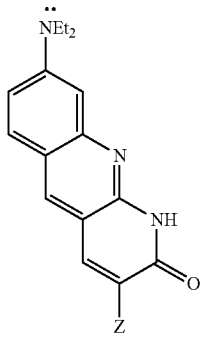

1

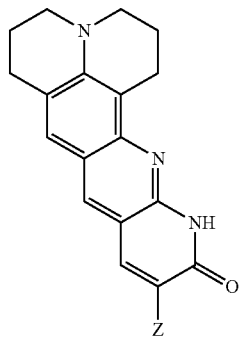

2

3

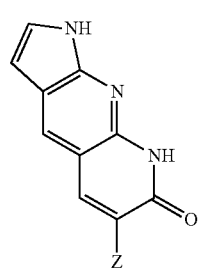

4

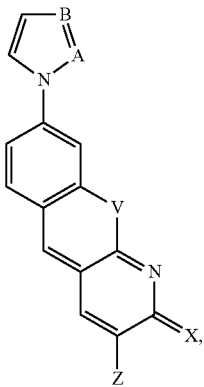

5 wherein A and B are each independently O, N, or S;
X is O, N, or S;
V is O, N, or S; and
Z is a furan, ribose, 2'-deoxyribose,

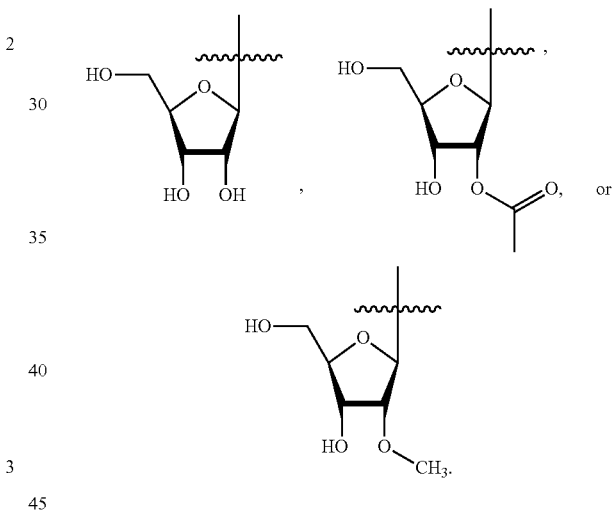

In other embodiments, the compound is one of compounds 6-8:

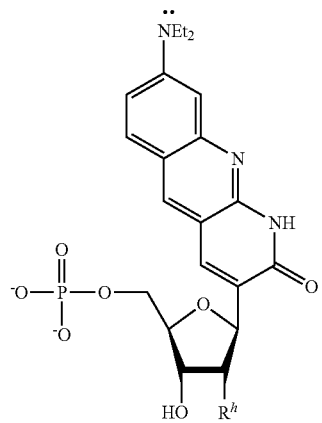

6

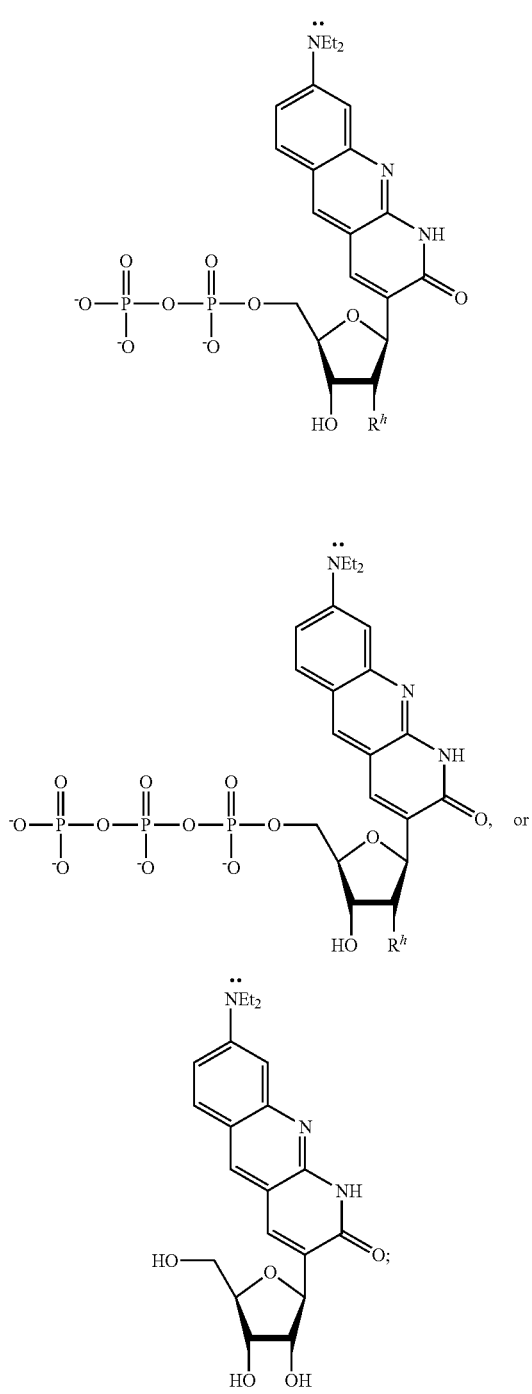

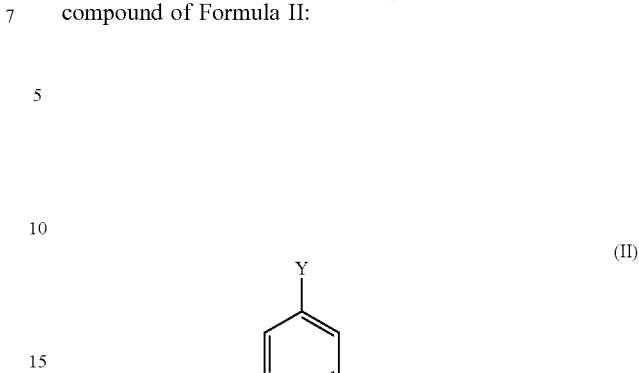

wherein $R^h$ is H or OH.

In various embodiments, the term "monosaccharide" includes various dehydrated or dehydroxylated derivatives of monosaccharides. In some embodiments, X is O. In some other embodiments, Y is $NR^bR^c$. In yet other embodiments, $R^b$ and $R^c$ are methyl or ethyl. In additional embodiments, Z is a furanose, ribose, deoxyribose, or deoxypyranose. In other embodiments, the Z is 2-hydroxymethyl-3-hydroxytetrahydrofuran-5-yl. In further embodiments, G is H. In other embodiments, $R^3$, $R^4$, $R^5$ and $R^6$ are each independently H, F, or $CF_3$.

In other embodiments, the compound of Formula IA is a compound of Formula II:

wherein $R^1$ and $R^2$ are each independently H, —($C_1$-$C_6$)alkyl, —($C_1$-$C_{12}$)alkyl, monophosphate, diphosphate, triphosphate, a phosphoramidite, or a protecting group. The protecting group can be a suitable silyl group, ether group, acetyl group, and the like known to persons skilled in the art. In various embodiments, $R^1$ and $R^2$ are each independently H, 4,4'-dimethoxytrityl (DMTr), or (2-cyanoethyl)-N,N-diisopropylphosphoramidityl.

In various embodiments, X is O and Y is $N(CH_2CH_3)_2$. In additional embodiments, $R^1$ and $R^2$ are H. In yet other embodiments, the compound of Formula IA is 7', 11, 12, or ABN:

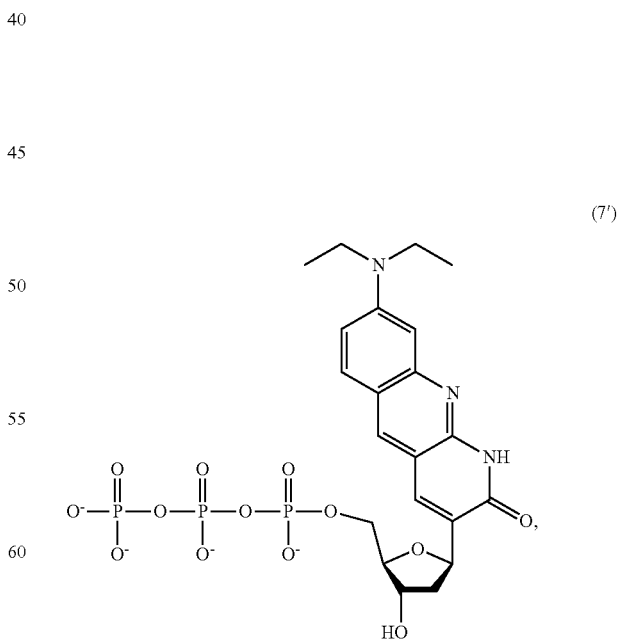

((2R,3S,5R)-5-(8-(diethylamino)-2-oxo-1,2-dihydrobenzo[b][1,8]naphthyridin-3-yl)-3-hydroxytetrahydrofuran-2-yl)methyl triphosphate -continued (11)

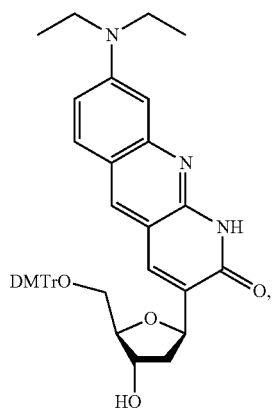

3-((2R,4S,5R)-5-((bis(4-methoxyphenyl)(phenyl)methoxy)methyl)-4-hydroxytetrahydrofuran-2-yl)-8-(diethylamino)benzo[b][1,8]naphthyridin-2(1H)-one (12)

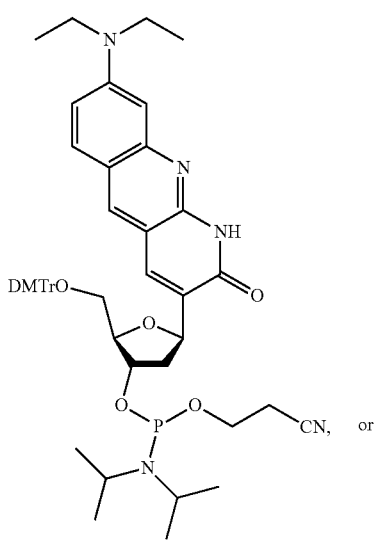

(2R,3S,5R)-2-((bis(4-methoxyphenyl)(phenyl)methoxy)methyl)-5-(8-(diethylamino)-2-oxo-1,2-dihydrobenzo[b][1,8]naphthyridin-3-yl)tetrahydrofuran-3-yl (2-cyanoethyl) diisopropylphosphoramidite (ABN)

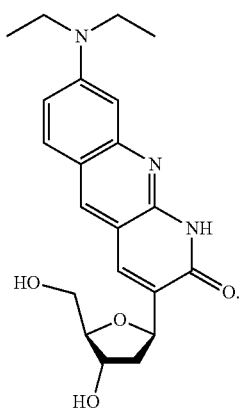

8-(diethylamino)-3-((2R,4S,5R)-4-hydroxy-5-(hydroxymethyl)tetrahydrofuran-2-yl)benzo[b][1,8]naphthyridin-2(1H)-one Also, this disclosure provides a method for imaging comprising:

a) incorporating into an oligonucleotide a compound of Formula IA:

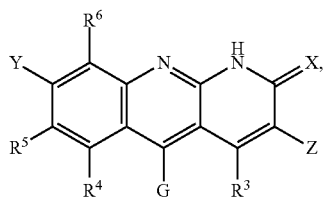

(IA)

or a salt thereof;
wherein
X is O, S, or $NR^a$, wherein $R^a$ is H or —$(C_1$-$C_{12})$alkyl;
Y is $NR^bR^c$, $OR^d$, $SR^e$, or

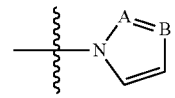

wherein A and B are each independently O, N, or S;
G is H, halo, or —$(C_1$-$C_{12})$alkyl;
$R^b$, $R^c$ $R^d$, and $R^e$ are each independently H or —$(C_1$-$C_{12})$alkyl;
$R^3$, $R^4$, $R^5$ and $R^6$ are each independently H, halo, OH, SH, $NH_2$, or —$(C_1$-$C_{12})$alkyl; and
Z is a monosaccharide;
wherein each —$(C_1$-$C_{12})$alkyl moiety is unbranched or branched, saturated or partially unsaturated, and substituted optionally with one or more halo, OH or $NH_2$;

b) exciting the base-paired compound at a suitable wavelength to form a fluorescing compound, wherein one or more photons excite a single molecule of the base-paired compound; and c) counting the number of photons emitted by the fluorescing compound as a function of time;
wherein the base-paired compound is thereby imaged.

In various embodiments, the compound is base-paired to a nucleic acid or oligonucleotide via hydrogen bonding. In various embodiments, the oligonucleotide is DNA or RNA. In various embodiments, the compound of Formula IA is ABN, as disclosed herein. In various embodiments, the monosaccharide group (Z) of the compound is covalently bound to one or more nucleic acids of the oligonucleotide via one or more phosphodiester groups. In various embodiments, the monosaccharide is covalently bound to the nucleic acid via one or more phosphate-deoxyribose moieties of the nucleic acid.

In various embodiments, a monosaccharide (Z) of Formula IA comprises a phosphate group and said monosaccharide is covalently bound at one end to a nucleic acid via a deoxyribose moiety and another end via a phosphate-deoxyribose moiety. In various embodiments, the compound of Formula IA is covalently lined to one or more nucleic acids via a phosphodiester group or phosphorothioate group.

In various embodiments, the method further comprises scavenging oxygen in a mixture comprising an oxygen scavenger and the incorporated compound. In other embodiments, the oxygen scavenger comprises buffer, Trolox, glucose oxidase, catalase, glucose, or a combination thereof. In other embodiments, the oxygen scavenger comprises protocatechuic acid (PCA), protocatechuate-3,4-dioxygenase (PCD), or a combination thereof. In other embodiments, the ratio of catalase (U/ml) to glucose oxidase (U/ml) is about 11:1 to about 15:1.

In various embodiments, the method further comprises contacting a compound of Formula IA and a nucleotide or oligonucleotide under suitable conditions for oligonucleotide synthesis wherein the synthesis proceeds in the 3'- to 5'-direction and the compound is covalently bound to the nucleotide or oligonucleotide. In various embodiments, oligonucleotide synthesis comprises solid-phase synthesis or enzymatic synthesis.

In various embodiments, the compound of Formula IA is a compound of Formula II (above), wherein $R^1$ and $R^2$ are each independently H, —($C_1$-$C_{12}$)alkyl, triphosphate, a phosphoramidite, or protecting group. In various embodiments, the compound is (2R,3R,5R)-2-((bis(4-methoxyphenyl) (phenyl)methoxy)methyl)-5-(8-(diethylamino)-2-oxo-1,2-dihydrobenzo[b][1,8]naphthyridin-3-yl) tetrahydrofuran-3-yl (2-cyanoethyl) diisopropylphosphoramidite (12).

In other various embodiments, the base-paired compound has an absorption wavelength that is blue- or red-shifted by at least 50 nanometers compared to its emission wavelength. In other embodiments, the blue- or red-shift is about 25 nanometers to about 250 nanometers, about 75 nanometers, about 100 nanometers, about 150 nanometers, or about 200 nanometers.

In further embodiments, the suitable wavelength to excite (i.e., absorption wavelength) the base-paired compound is about 415 nanometers to about 445 nanometers. In other embodiments, the wavelength for excitation is about 375 nanometers to about 525 nanometers, about 400 nanometers, about 425 nanometers, about 450 nanometers, about 475 nanometers, or about 500 nanometers.

In various embodiments, the single molecule of the base-paired compound is excited by one or more photons, 1-5 photons, 1 photon, 2 photons, 3 photons, 4 photons, 5 photons, 6 photons, 7 photons, 8 photons, 9 photons, or 10 photons.

In various other embodiments, the fluorescing compound has an emission wavelength of about 470 nanometers to about 545 nanometers, about 400 nanometers to about 600 nanometers, about 450 nanometers, about 480 nanometers, about 500 nanometers, about 520 nanometers, about 540 nanometers, about 560 nanometers, or about 580 nanometers.

In some embodiments, the based-paired compound is imaged by fluorescence correlation spectroscopy, fluorescence spectroscopy, single-molecule fluorescence spectroscopy, Förster resonance energy transfer (FRET), or single-molecule FRET. In other embodiments, a single molecule of the fluorescing compound emits a sufficient number of photons to be imaged by fluorescence correlation microscopy. In other embodiments, a sufficient number of emitted photons is 1 to about 50 photons, 2 photons, about 5 photons, about 10 photons, about 20 photons, or about 30 photons. In yet other embodiments, the rate of photons emitted by a single molecule of the fluorescing compound is about 6 kilohertz to about 8 kilohertz, about 4 kilohertz to about 10 kilohertz, about 5 kilohertz, about 7 kilohertz, or about 9 kilohertz. In various embodiments, ABN is detected at the single molecule level in double-stranded DNA using smTIRF.

Results and Discussion

Synthesis. The synthesis of ABN starts with the construction of the bicyclic ring 2-chloro-7-(diethylamino)quinoline-3-carbaldehyde 2 by the reaction of 3-(diethylamino)acetanilide with the Vilsmeier reagent. The electron donating nature of the diethylamino group renders selective formation of the singly formylated product difficult to achieve, but careful temperature control allows for an adequate yield at multi-gram scale. The quinoline ring 2 undergoes $S_NAr$ and cyclization with sodium azide to give a tricyclic compound 3 and the tetrazole ring is then opened reductively by triphenylphosphine in 2 N HCl at reflux to give 2-amino-7-(diethylamino)quinoline-3-carbaldehyde 4. Adding the Wittig reagent ethyl 2-bromo-2-(triphenylphosphoranylidene) acetate 8 (synthesized by the bromination of ethyl (triphenylphosphoranylidene) acetate) to compound 4 yields the brominated tricyclic nucleobase precursor 5. A Heck reaction of 5 with 3',5'-O-TBS dihydrofuran 10 using palladium acetate and triphenylarsine followed by desilylation with acidic tetrabutylammonium fluoride gives 3'-keto nucleoside 6. This Heck reaction is selective for the face, owing to the steric influence of the 3'-O-TBS group, as usual in the synthesis of C-ribosides. Stereoselective reduction of 6 with sodium triacetoxyborohydride completes the ABN nucleoside 7. The β configuration of the anomeric C is verified by its hydrogen's coupling constants $^3J_{H,H}$=5.9 and 10.0 Hz. A comparison of $^{13}$C NMR shifts—the carbonyl at δ=165.0 ppm for ABN in $CD_3OD$ is especially diagnostic—with published data for simpler 1,8-naphthyridin-2(1H)-one nucleoside analogues indicates that ABN is present only in the thymidine-like tautomeric form as shown (Scheme 1), to the limit of detection by NMR. Computational prediction of the NMR spectra (MP2/cc-pVDZ/COSMO) confirms this assignment. B3LYP and MP2 calculations using three different basis sets, with and without solvation, predict the T-like tautomer to be 10.3-13.8 kcal mol$^{-1}$ more stable than the cytidine-like tautomer. Dimethoxytritylation followed by 3'-phosphoramidite installation under standard conditions prepares the nucleotide for solid-phase oligonucleotide synthesis (Scheme 2).

Scheme 1.

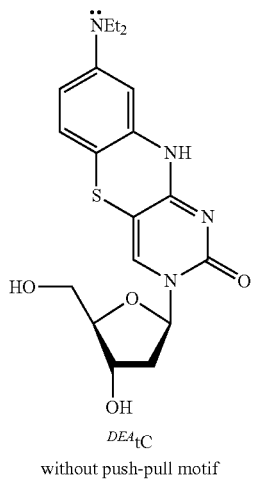

$^{DEA}$tC
without push-pull motif

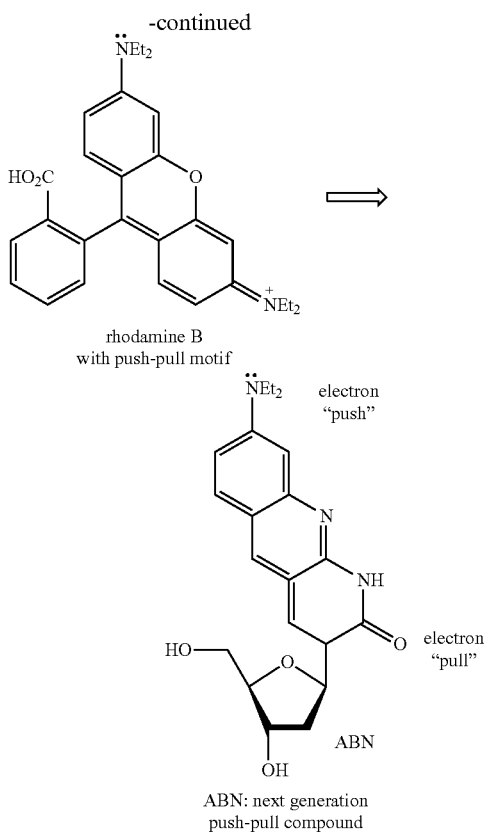

ABN: next generation push-pull compound

Push-pull motifs are hallmarks of bright organic fluorophores but are rare in fluorescent nucleotides. The redesign of a nucleoside analogue to include this motif significantly increases ε and $\Phi_{em}$, enabling robust single-molecule detection.

Oligonucleotide design and preparation. To assess ABN's photophysical properties and natural base mimicry in oligonucleotides, we designed and prepared a hairpin ODN1 and two 10-mer sequences ODN4 and ODN7 that provide a representative set of local environments (FIG. 1). The hairpin was designed to place ABN at the third position of a six-residue loop, a site that is not conducive to base stacking and is expected to leave the nucleobase predominantly solvent exposed. ODN4 and ODN7 were selected to provide a first look at neighboring base effects on ABN's fluorescence. By annealing these ODNs to matched and mismatched complementary strands, the base pairing of ABN and its effects on fluorescence can be measured.

Figure 2:
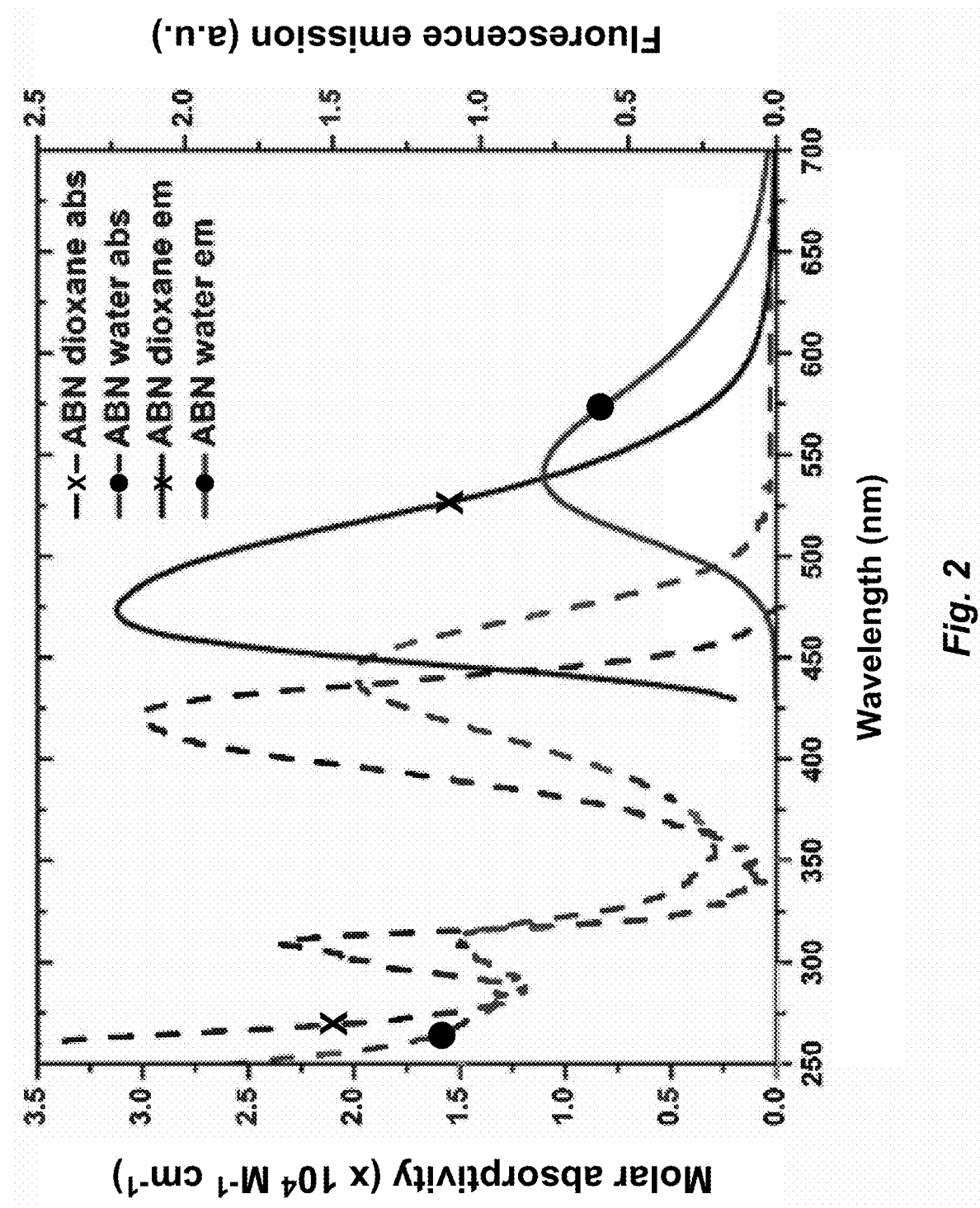
FIG. 2. Absorption (dashed line) and emission (solid line) spectra of ABN in dioxane (taller solid line) and water (shorter solid line). The integral areas of emission spectra are normalized to brightness $\varepsilon\Phi_{em}$.

Photophysical properties. Steady-state measurements. Steady-state absorption and fluorescence measurements of ABN in water, 1x PBS buffer (pH 7.4), 1,4-dioxane, and mixtures indicate that it is among the brightest fluorescent nucleosides reported to date ($\varepsilon_{442}$=20 000 M$^{-1}$ cm$^{-1}$ and $\Phi_{em,540}$=0.39 in water and ($\varepsilon_{420}$=30 000 M$^{-1}$ cm$^{-1}$ and $\Phi_{em,474}$=0.64 in 1,4-dioxane; Table 1; FIG. 2). Next to its closest competitors on brightness, pentacyclic adenine pA ($\Phi_{387}$=15 300 M$^{-1}$ cm$^{-1}$ and $\Phi_{em,420}$=0.66 in water) and a coumarin nucleoside ($\Phi_{315}$=38 000 M$^{-1}$ cm$^{-1}$ and $\Phi_{em,455}$=0.11 in water), the absorption and emission of ABN in aqueous solution are red-shifted by more than 50 and 80 nm, respectively. Owing to the conjugated push-pull system in the design of ABN, the absorption and emission wavelengths are the longest known for a FBA designed to be capable of Watson-Crick hydrogen bonding. Recorded emission spectra in water using excitation wavelengths ranging from 310-500 nm are nearly superposable, as are excitation spectra recorded for emission wavelengths spanning 500-650 nm. These observations support the predominance of a single tautomeric form in dilute, aqueous solution.

TABLE 1

Steady-state fluorescence data for the ABN nucleoside

| Solvent | $\lambda_{ex, max}$ (nm) | $\lambda_{em, max}$ (nm) | ε at $\lambda_{ex, max}$ (M$^{-1}$ cm$^{-1}$) | $\Phi_{em}$ | ε · $\Phi_{em}$ |
|---|---|---|---|---|---|
| H$_2$O | 442 | 540 | 2.0 × 10$^4$ | 0.39 | 7800 |
| 1 × PBS pH 7.4 | 442 | 540 | n.d.$^a$ | 0.39 | — |
| 1,4-dioxane | 420 | 474 | 3.0 × 10$^4$ | 0.64 | 19000 |

$^a$n.d. ¼ not determined.

Next, we measured the fluorescence of ABN in single-stranded and duplex DNA oligonucleotides to determine how base pairing and stacking influence its photophysical properties (Table 2). ABN increases its fluorescence to $\Phi_{em}$=0.50-0.53 in matched duplex DNA oligonucleotides when base paired with A and $\Phi_{em}$=0.55 when the analogue is present in the hairpin loop of ODN1. The quantum yield is less, 0.40 and 0.29, in ODN1:ODN3 and ODN4:ODN6 respectively, in which ABN is base paired with G. In ODN7:ODN9 $\Phi em$,=0.55, slightly greater than when base paired with A. In all of these single-stranded and duplex sequences, ABN is brighter than any other known FBA when present in oligonucleotides.

Temperature-dependent circular dichroism measurements of all six duplexes are consistent with the B-DNA conformation with only minimal perturbation (Table 2). Except in the ODN1 hairpin, where ABN is expected to be mostly solvent exposed, the melting temperatures of the duplexes are typically somewhat depressed as compared with their natural counterparts. Duplex stability is lowest when ABN has 5'-G and 3'-C neighbors, an observation consistent with other tricyclic FBAs, especially those that are electron-rich. The observed melting temperatures provide little indication of whether ABN is a better T- or C-surrogate.

Solution NMR studies of the free nucleoside and computation clearly indicate a preferred tautomer with an acceptor-donor-acceptor hydrogen bonding pattern as in thymine, as discussed above. It is possible that ABN forms wobble base pairs with G or base pairing with G drives tautomerism to a C-like donor-acceptor-acceptor hydrogen bonding pattern.

TABLE 2

Steady-state photophysical data for ABN in DNA oligonucleotides

| Oligo$^a$ | $\lambda_{abs, max}$ (nm) | $\lambda_{em, max}$ (nm) | $\Phi_{em}$ | $T_m$/° C. | $\Delta T_m^{b}$/° C. |
|---|---|---|---|---|---|
| ODN1 | 450 | 530 | 0.55 | 63.6 ± 0.6 | +3.1 |
| ODN1:ODN2 | 440 | 530 | 0.53 | 61.8 ± 0.4 | −4.7 |
| ODN1:ODN3 | 468 | 523 | 0.40 | 61.3 ± 0.6 | +1.6$^c$ |
| ODN4 | 452 | 540 | 0.49 | — | — |
| ODN4:ODN5 | 440 | 525 | 0.51 | 39.9 ± 0.3 | −0.5 |
| ODN4:ODN6 | 470 | 523 | 0.29 | 41.3 ± 0.3 | −7.3$^c$ |
| ODN7 | d | 532 | 0.62 | — | — |
| ODN7:ODN8 | d | 532 | 0.50 | 34.3 ± 0.3 | −14.1 |
| ODN7:ODN9 | d | 532 | 0.55 | 37.9 ± 0.3 | −11.8$^c$ |

$^a$Oligonucleotide sequences are given in FIG. 1.
$^b\Delta T_m$ = $T_m$ for ABN-containing duplex listed in the table row − $T_m$ for the corresponding duplex with canonical thymidine in place of ABN.
$^c$Comparison with $T_m$ for the corresponding natural duplex with a C:G base pair.
d $\lambda_{ex, max}$ is concentration-dependent; see FIG. 6.

Figure 6:
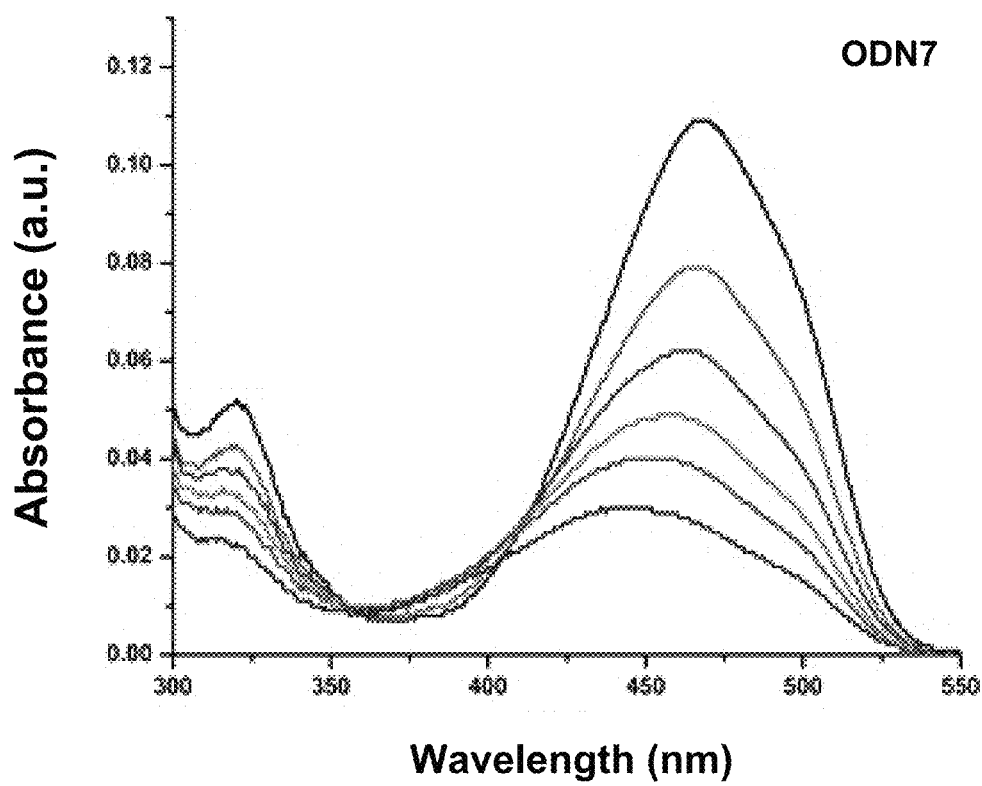
FIG. 6. Absorption spectra of ODN7, ODN7:ODN8 and ODN7:ODN9 at different concentrations in 1×PBS buffer (pH 7.4).
Figure 6:
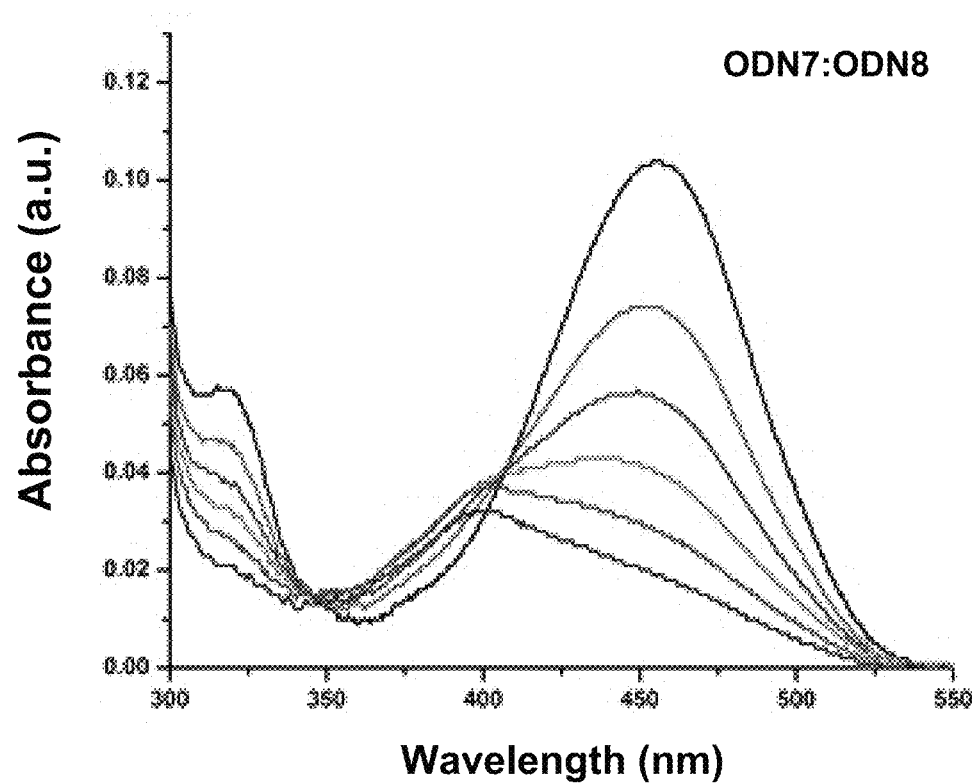
Figure 6:
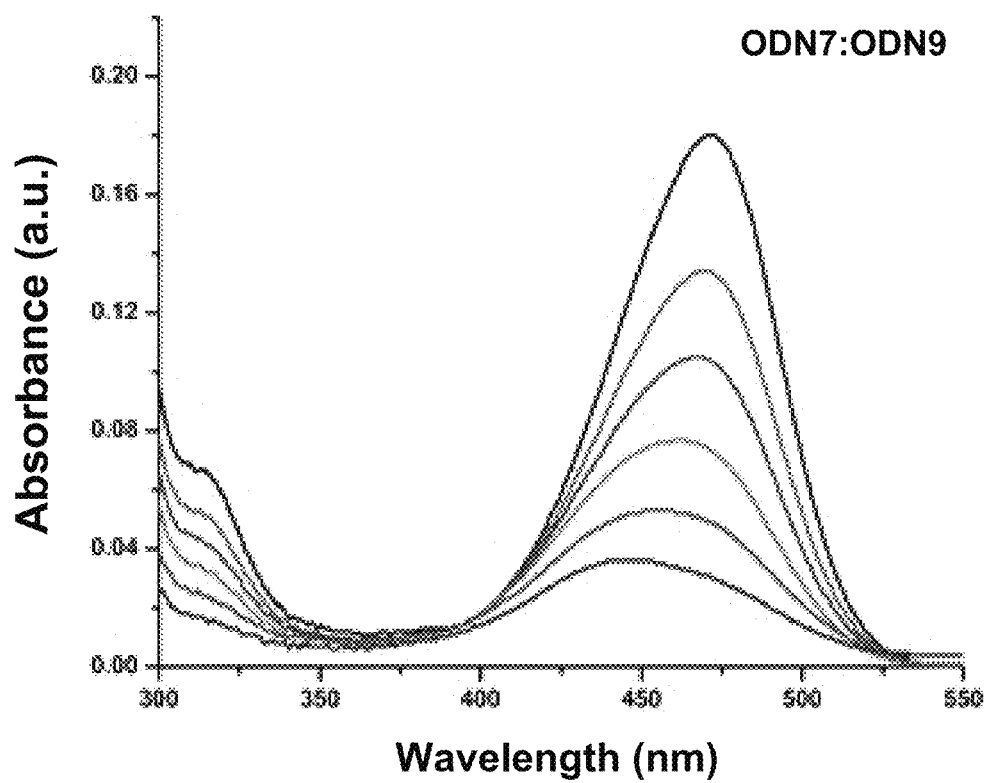

The Stokes shift is shortened in ABN:G pairs, resulting mostly from red-shifted absorption relative to what is observed in ABN:A pairs. Computational studies (B3LYP/cc-pVDZ) predict that the C-like tautomer will absorb at approximately 45 nm longer wavelength than the T-like tautomer. These calculations are consistent with a tautomeric base pair with G that retains high fluorescence but is indicated by changed $\lambda_{ex}$. The absorption spectra of ODN7 alone and in the ODN7:ODN8 and ODN8:ODN9 duplexes are concentration dependent (FIG. 6). This dependency indicates a significant potential for change in the local environment around ABN and possibly the analogue's tautomeric state in these sequence contexts.

Single-molecule fluorescence measurements. Given the very attractive bulk-level photophysical properties of ABN in solution, we next investigated its potential as a single-molecule probe. Recent studies have demonstrated multiphoton excitation as a promising approach to the sensitive detection of fluorescent base analogues. Two-photon excitation of pA in oligonucleotides allowed detection close to the single-molecule level, whereas one-photon (1P) excitation resulted in rapid photobleaching. In a later study, the base analogue DMA$^{th}$aU was detected as a free nucleoside at the single-molecule level for the first time via multiphoton excitation with a brightness of ~7 kHz per molecule following three-photon excitation (see *Phys. Chem. Chem. Phys.*

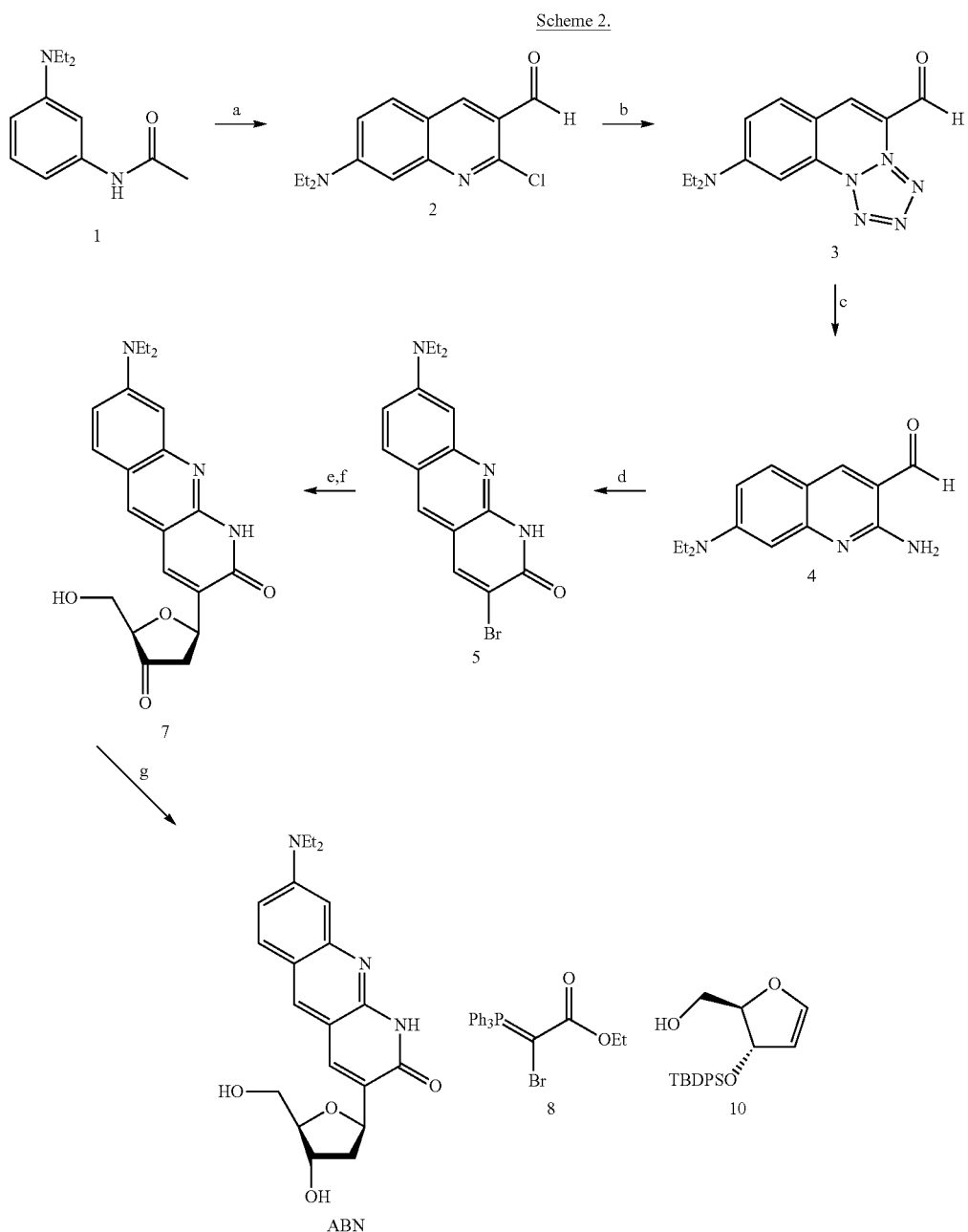

Scheme 2.

Synthesis of ABN nucleoside analogue. Reagents and conditions: (a) DMF, POCl$_3$, 50° C., 20 min (15%). (b) NaN$_3$, DMF, 90° C., 18 h (85%). (c) PPh$_3$, 2N HCl, reflux, 2 h (70%). (d) 8, NaOEt, ethanol, 70° C., 4 h. (e) 10, AsPh$_3$, Pd(OAc)$_2$, 60° C., 18h. (f) TBAF, AcOH, rt, 1 h. (g) NaBH(OAc)$_3$, AcOH, 0° C., 1 h (9% over 4 steps).

Figure 3:
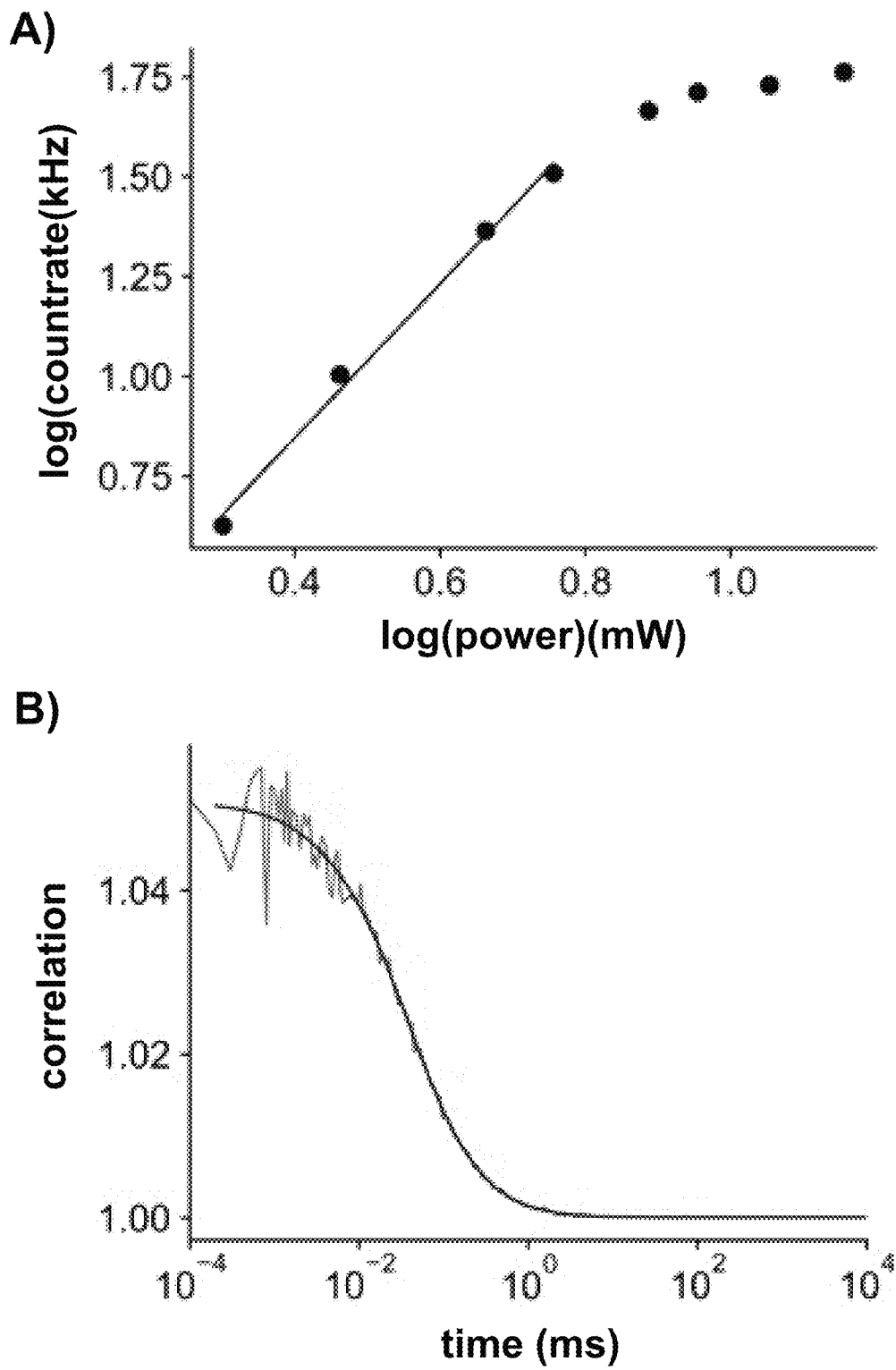
FIG. 3. 2P single-molecule characterization of ABN. A) logarithmic plot of the power dependence of the emission intensity. The first four points show a linear behavior with a slope of 1.9; the slope changes for powers higher than 5.7 mW, presumably due to saturation effects. B) FCS measurement (wavy line) and fit to the data (smooth line). The fit gives an average of 7 molecules in the focus which leads to an average count rate per molecule of 7±0.5 kHz/molecule. The excitation power for FCS was 11 mW. All measurements were done with a 100 nM ABN solution in TRIS buffer.

2018, 20 (45), 28487; and *J. Phys. Chem. Lett.* 2019, 10 (17), 5008). Using an experimental setup consisting of a broadband ultrafast laser with dispersion compensation, we found that ABN could be optimally excited via a 2P process (FIG. 3A). The 2P brightness was measured using fluorescence correlation spectroscopy (FCS) and found to match that of DMA$^{th}$aU at 7 kHz per molecule (FIG. 3B). Importantly, unlike DMA$^{th}$aU, which was predominately (96%) in a dark state, a controlled dilution suggests that ABN is exclusively in a bright state, which we attribute to the single tautomer observed by NMR (see above).

Figure 4:
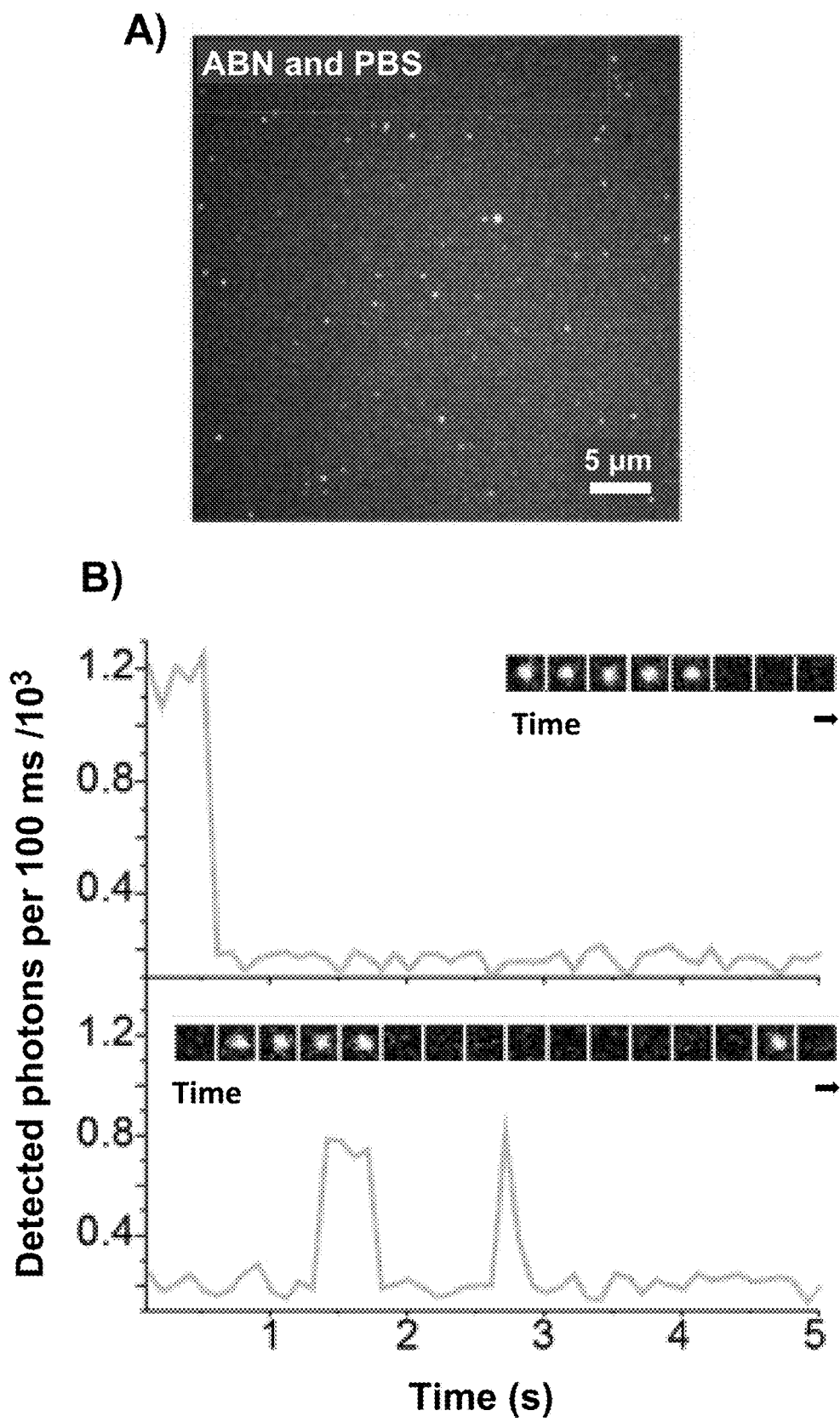
FIG. 4. 1P single-molecule characterization of ABN. A) Average fluorescence intensity projection of a 15 s movie of single ABN molecules adsorbed onto a glass surface. B) Fluorescence intensity as a function of time of two single ABN molecules, with subselections of the traces shown as time montages (inset, scale bar=200 nm). C) A histogram showing the distribution of the total number of photons detected from single ABN emitters, μ=5300±1800 photons determined from a log-normal distribution fit. D) A histogram showing the mean number of photons detected/frame for single ABN emitters, μ=1500±600 photons/100 ms, determined from a log-normal distribution fit. (N=2402 molecules).
Figure 4:
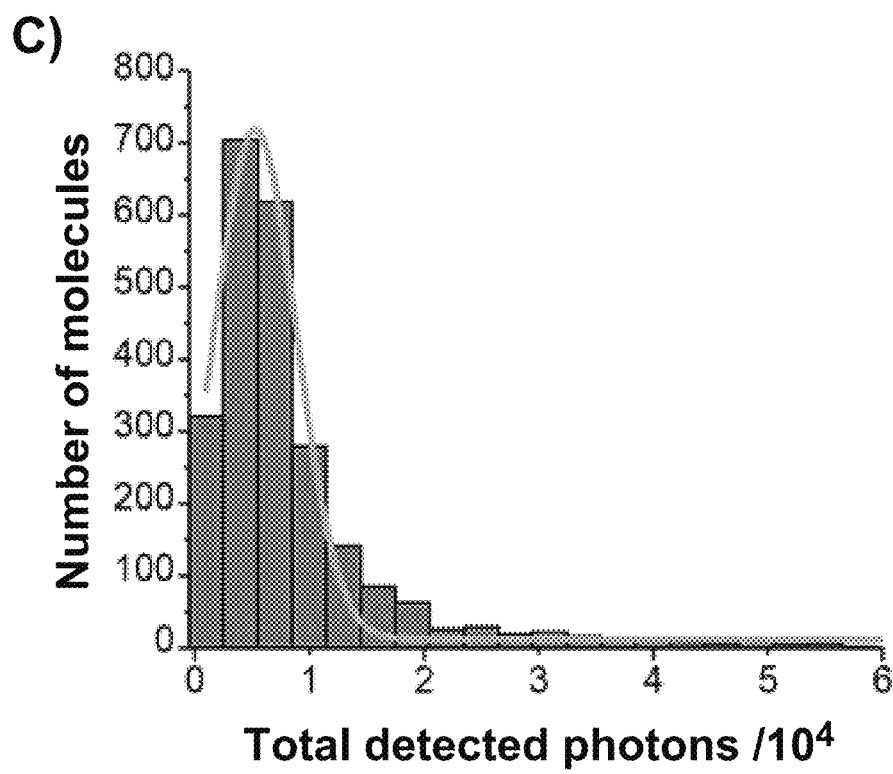
Figure 4:
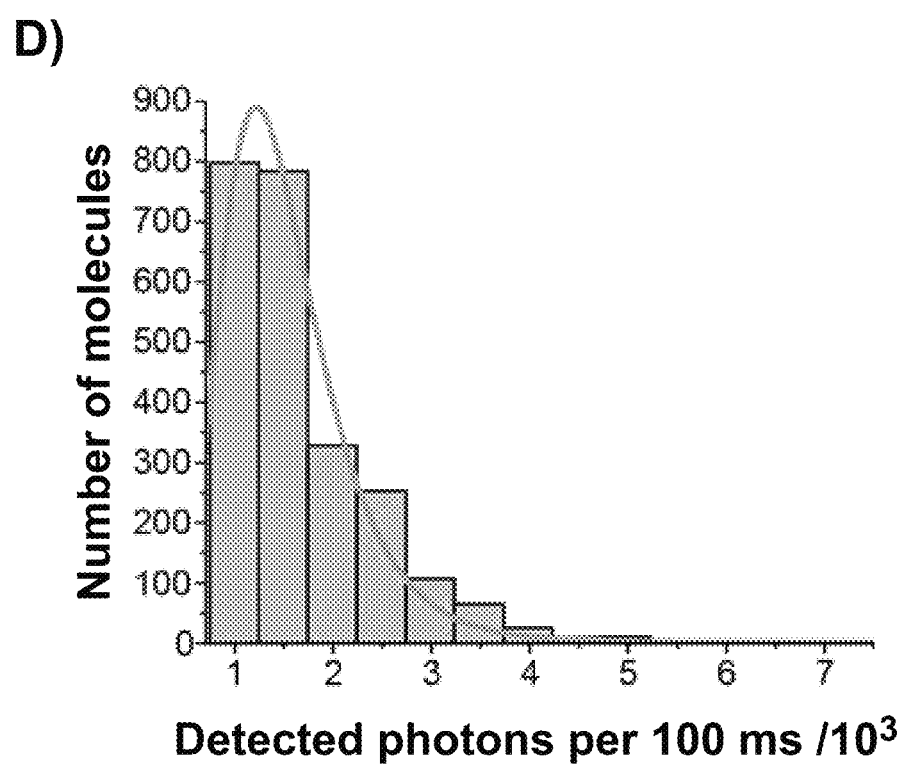
Figure 5:
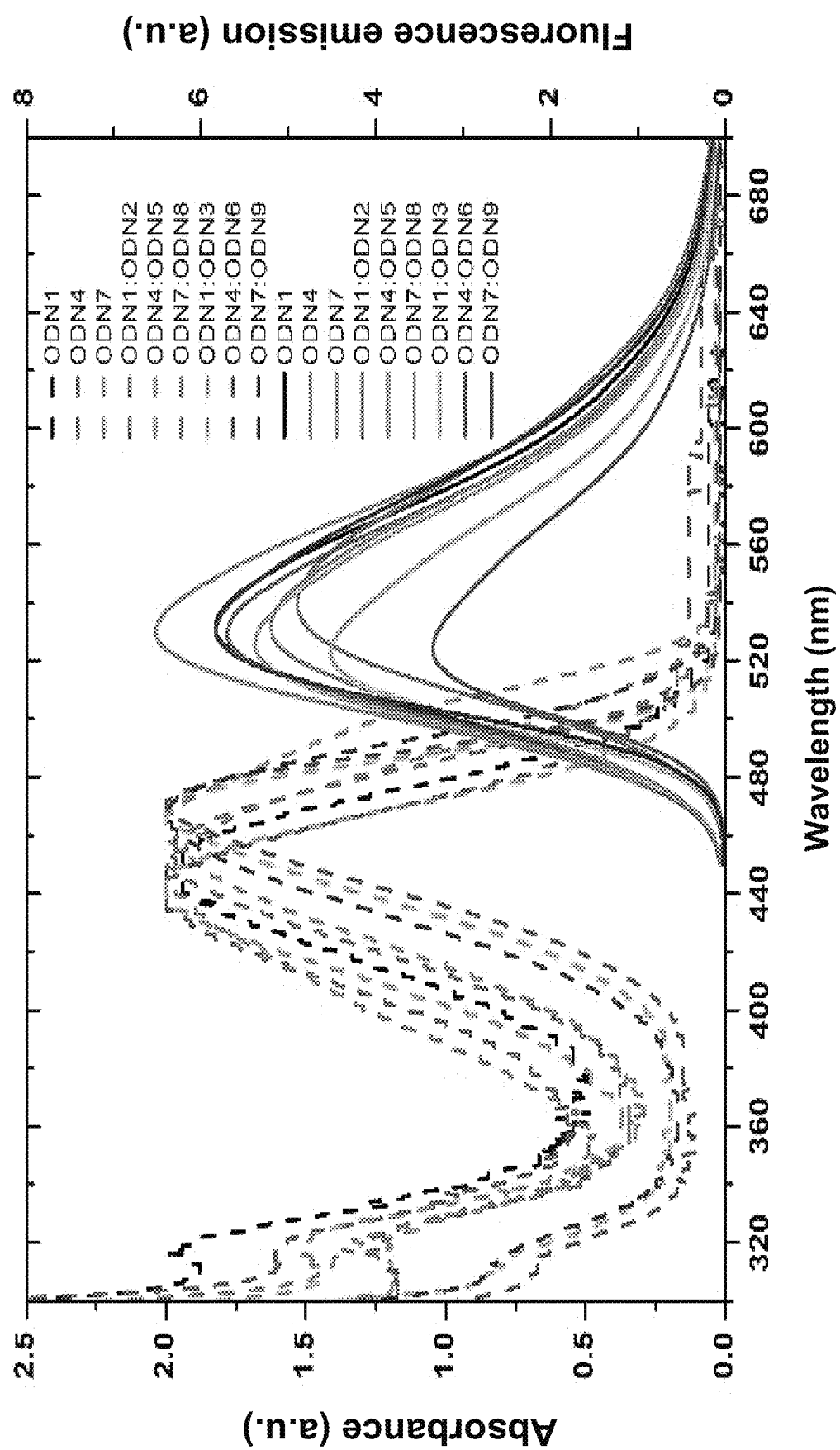
FIG. 5. Absorbance (dashed line) and emission (solid line) spectra of ABN-modified oligonucleotides in 1×PBS buffer (pH7.4).

The red-shifted absorption profile, high 2P brightness and predominance of the bright state made ABN a promising candidate for single-molecule detection via 1P excitation. We found that spatially isolated individual molecules of ABN randomly dispersed on a glass coverslip could be readily visualized using single-molecule total internal reflection fluorescence (smTIRF) microscopy (FIG. 4A). Furthermore, these fluorescent puncta underwent single-step photobleaching under constant irradiation (FIG. 4B), consistent with the idea that ABN has suitable optical properties to be used as a single-molecule fluorescent nucleoside. By quantifying >2000 individual trajectories, we were able to determine the mean total detected photon value of 5300±1800 photons per molecule; furthermore, a mean of 1500±600 photons were detected per 100 ms integration from each molecule at a power density of 0.2 kW cm$^{-2}$. Combined, these data suggest that the mean total on-time of ABN was 0.35±0.18 s under these conditions. The similarities in brightness following 1P and 2P excitation (15 kHz and 7 kHz per molecule, respectively), show that ABN has excellent photostability under both excitation regimes.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Synthesis of ABN

General Experimental.

Starting materials were obtained in ACS reagent grade or higher from Acros Organics, Alfa Aesar, Fisher Scientific, Sigma-Aldrich and Wako Chemicals; and used without further purification. Analytical thin-layer chromatography was performed on pre-coated 200 µm silica gel F-254 plates. Visualization was performed by ultraviolet light. Flash column chromatography was performed using a Teledyne-Isco CombiFlash RF 200 using UV/vis detection. $^1$H NMR spectra were recorded on 400 and 500 MHz Varian spectrometers using an AutoX PFG probe at 298 K; residual solvent peaks were used as internal references: DMSO (quint, δH=2.50 ppm), CHCl$_3$ (s, δH=7.26 ppm) or methanol (quint, δH=3.31 ppm). $^{13}$C NMR spectra were recorded on 400 and 500 MHz Varian spectrometers using an AutoX PFG probe at 298 K; δ relative to DMSO (δ 40.50 ppm), CHCl$_3$ (δ 77.23 ppm) or methanol (δ 49.00 ppm). Coupling constants (J) are reported in hertz (Hz). The following abbreviations are used to describe the multiplicities: s=singlet, d=doublet, t=triplet, q=quartet, quint=quintet, sext=sextet, m=multiplet, dd=doublet-doublet, ddd=doublet-doublet-doublet, dt=doublet-triplet, dq=doublet-quartet. High-resolution electrospray ionization (ESI) mass spectrometry was performed using an Agilent 6530 Accurate-Mass Q-TOF LC/MS.

Scheme 3.

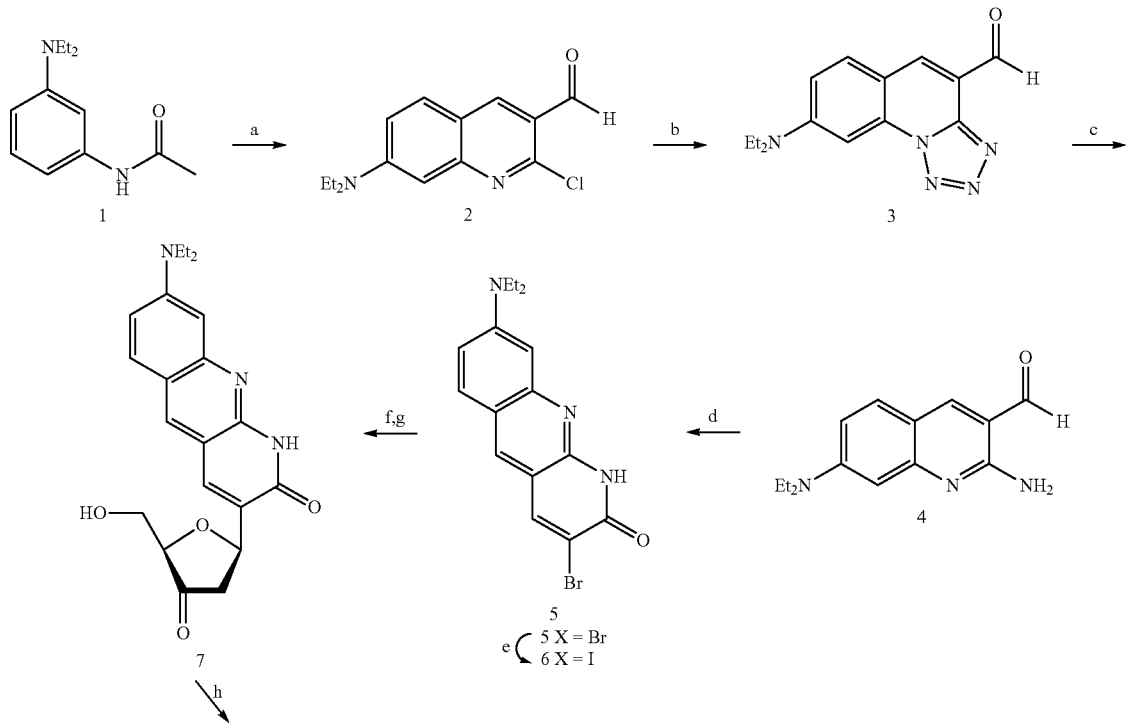

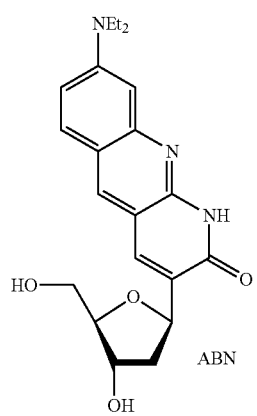

ABN

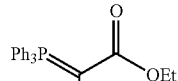

8

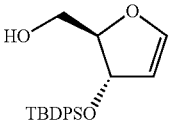

10

Modified synthesis of the ABN nucleoside. Reagents, conditions, and yields: (a) DMF, POCl₃, 50° C., 20 min (15%). (b) NaN₃, DMF, 90° C., 18 h (85%). (c) PPh₃, 0.5N HCl, reflux, 2 h (70%). (d) 8, dioxane, 100° C., 4 h (25%). (e) NaI, CuI, trans-N,N′-dimethylcyclohexane-1,2-diamine, dioxane, 110° C., 18 h (90%). (f) 11, AsPh₃, Pd(OAc)₂, NBu₃, 60° C., 18 h. (g) TBAF, AcOH, rt, 1 h (50% over 2 steps). (h) NaBH(OAc)₃, AcOH, ACN, 0° C., 1 h (80%).

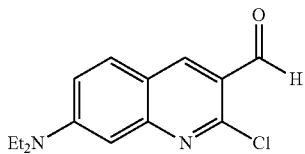

2

2-chloro-7-(diethylamino)quinoline-3-carbaldehyde (2). POCl3 (27.1 mL, 291 mmol) is placed into a dry flask under nitrogen and cooled in an ice bath, and to this, DMF (5.60 mL, 72.7 mmol) is added portionwise while stirring. 3-(diethylamino)acetanilide (5.00 g, 24.2 mmol) in 1,4-dioxane (7.00 mL) is added to the mixture, and the reaction is heated at 50° C. After 20 min, the reaction mixture is quenched by transferring it portionwise to a solution of cold saturated. NaHCO₃. NaOH pellets and ice are added to the bath with stirring until the mixture is alkaline (pH 9). The slurry is filtered and the solid is washed with water then dissolved in DCM and dried over Na₂SO₄ and evaporated to dryness to collect the crude product. These crude products are purified by automated flash chromatography (0-100% EtOAc in hexane) and the product elutes with 30% EtOAc in hexane (R$_f$=0.652). The solid is recrystallized using DCM and hexane to give 956 mg (15.0% yield) of yellow solid (2).1
¹H NMR (400 MHz, CDCl3) δ 10.30 (s, 1H), 8.35 (s, 1H), 7.61 (d, J=9.2 Hz, 1H), 7.02 (dd, J=9.2, 2.6 Hz, 1H), 6.90 (d, J=2.5 Hz, 1H), 3.45 (q, J=7.1 Hz, 4H), 1.21 (t, =7.1 Hz, 6H). ¹³C NMR (125 MHz, CDCl₃) δ 188.8, 152.1, 151.8, 151.4, 138.8, 131.2, 121.7, 118.4, 116.5, 104.4, 45.0, 12.5. HR-ESI MS (m/z): [M+H]⁺ calculated for C₁₄H₁₆ClN₂O 263.0951, found 263.0963.

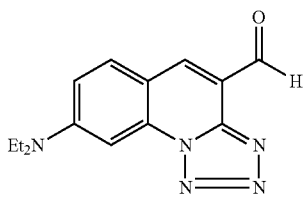

3

8-(diethylamino)tetrazolo[1,5-a]quinoline-4-carbaldehyde (3). (2) (3.00 g, 11.5 mmol) and sodium azide (2.23 gm, 34.4 mmol) are dissolved in 7.00 mL of DMF, then the reaction is heated and stirred at 80.0° C. The reaction is monitored by TLC (70% EtOAc in hexane) (R$_f$=0.64) and stopped after 24 hours. The reaction mixture is then added to iced water to induce precipitation. The solid is dissolved in 3.00 mL of DCM and induced to crystallize by the addition of 100 mL cold hexane. The solid is collected to give 2.95 g (95.0% yield) of yellow solid (3). ¹H NMR (500 MHz, CDCl₃) δ 10.50 (s, 1H), 8.31 (s, 1H), 7.78 (d, J=9.2 Hz, 1H), 7.57 (d, J=2.5 Hz, 1H), 7.00 (dd, J=9.2, 2.6 Hz, 1H), 3.59 (q, J=7.2 Hz, 4H), 1.32 (t, J=7.2 Hz, 6H). ¹³C NMR (500 MHz, CDCl₃) δ 186.2, 152.1, 146.9, 136.0, 135.0, 132.9, 114.7, 114.3, 112.4, 95.5, 45.4, 12.5. HR-ESI MS (m/z): [M+H]⁺ calculated for C₁₄H₁₆N₅O 270.1355, found 270.1365.

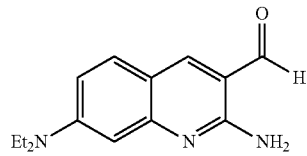

4

2-amino-7-(diethylamino)quinoline-3-carbaldehyde (4). (3) (1.00 gm, 3.72 mmol) and triphenylphosphine (1.95 gm, 7.44 mmol) are added to a round-bottom flask. 5.00 mL of methanol and 18.0 mL of 2.00 N HCl are added, and the reaction is heated at reflux, monitoring by TLC (5% methanol in DCM) (R$_f$=0.32). After 2 hours, the reaction is cooled to room temperature, ice water (200 mL) is added, and the mixture is filtered. 2.00 N NaOH is added portion-wise to the filtrate until yellow solid precipitates. The slurry is filtered, and the yellow solid is collected to give 633 mg (70.0% yield) of the product (4). ¹H NMR (400 MHz, CDCl₃) δ 9.79 (s, 1H), 8.00 (s, 1H), 7.47 (d, J=9.1 Hz, 1H), 6.78 (dd, J=9.1, 2.5 Hz, 1H), 6.61 (d, J=2.5 Hz, 1H), 3.47 (q, J=7.1 Hz, 4H), 1.23 (t, J=7.1 Hz, 6H). ¹³C NMR (400 MHz, CDCl₃) δ 191.4, 156.5, 152.8, 152.3, 146.9, 130.9, 115.0, 113.4, 112.1, 102.2, 44.9, 12.9. HR-ESI MS (m/z): [M+H]⁺ calculated for C₁₄H₁₈N₃O 244.1450, found 244.1461.

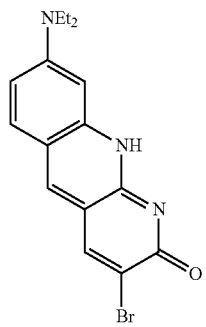

5

3-bromo-8-(diethylamino)benzo[b][1,8]naphthyridin-2 (10H)-one (5). (4) (300 mg, 1.23 mmol) and ethyl 2-bromo-2-(triphenylphosphoranylidene)acetate (791 mg, 1.85 mmol) are dissolved in 7.00 mL of ethanol, and 20% sodium ethoxide (840 µL, 2.47 mmol) is added and the reaction is heated at 70.0° C. The reaction is monitored by TLC (5% methanol in DCM) ($R_f$=0.52) and after 18 h, is cooled to room temperature. The solvent is evaporated under vacuum then automated flash chromatography is performed (0-100% DCM in EtOAc) and the product coelutes with triphenylphosphine oxide at 20% DCM in EtOAc. This crude product mixture is used directly in the next step.

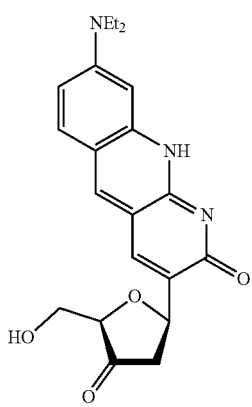

6

8-(diethylamino)-3-((2R,5R)-5-(hydroxymethyl)-4-oxo-tetrahydrofuran-2-yl)benzo[b][1,8]naphthyridin-2(10H)-one (6). Palladium acetate (15.6 mg, 0.0696 mmol) and triphenylarsine (42.6 mg, 0.139 mmol) are dissolved in 1.5 mL DMF and stirred for 30 min at room temperature. The reaction mixture is then transferred to another flask containing the crude product (5) (30 mg, 0.087 mmol) and (10) (59.9 mg, 0.174 mmol), then tributylamine (41.3 µL, 0.174 mmol) is added. The reaction is heated to 60.0° C. and monitored by TLC (50% DCM in EtOAc). After 18 h, the reaction is cooled to room temperature then 10 drops acetic acid and 1M tetrabutylammonium fluoride (0.174 mL, 0.174 mmol) are added and the reaction is stirred for 1 h at room temperature. The solvent is then evaporated under vacuum and automated flash chromatography is performed (0-100% EtOAc in hexane), with semi-pure product eluting at 90% EtOAc in hexane.

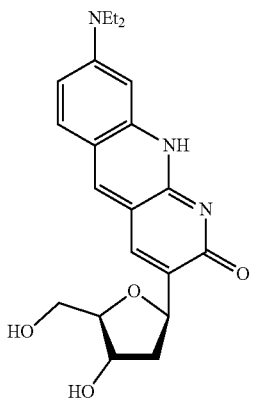

7

8-(diethylamino)-3-((2R,4R,5R)-4-hydroxy-5-(hydroxymethyl)tetrahydrofuran-2-yl)benzo[b][1,8]naphthyridin-2(10H)-one (7, ABN). The semi-pure product (6) and sodium triacetoxyborohydride (27.7 mg, 0.131 mmol) are dissolved in 0.50 mL acetonitrile and 0.50 mL acetic acid at 0° C. The reaction is stirred for 2 h at that temperature and monitored by TLC (10% methanol in DCM) ($R_f$=0.44). The solvent is then evaporated, and automated flash chromatography is performed with the product eluting at 10% methanol in DCM. The solvent is evaporated to give 10 mg (21.2% yield over the last 4 steps) of yellow solid (7). $^1$H NMR (500 MHz, MeOD) δ 8.29 (s, 1H), 8.07 (d, J=1.1 Hz, 1H), 7.74 (d, J=9.2 Hz, 1H), 7.16 (dd, J=9.3, 2.5 Hz, 1H), 6.88 (d, J=2.4 Hz, 1H), 5.24 (dd, J=10.0, 5.9 Hz, 1H), 4.33 (dt, J=5.5, 2.4 Hz, 1H), 3.99 (td, J=4.6, 2.9 Hz, 1H), 3.73 (qd, J=11.8, 4.6 Hz, 2H), 3.56 (q, J=7.1 Hz, 4H), 2.43 (ddd, J=13.1, 5.9, 2.1 Hz, 1H), 2.00-1.93 (m, 1H), 1.26 (t, J=7.1 Hz, 6H). $^{13}$C NMR (400 MHz, MeOD) δ 165.1, 151.9, 151.5, 149.8, 137.6, 136.2, 132.5, 130.9, 119.7, 116.4, 112.9, 103.3, 88.8, 77.3, 74.3, 64.0, 45.7, 42.6, 13.0. HR-ESI MS (m/z): [M+H]$^+$ calculated for $C_{21}H_{26}N_3O_4$ 384.1923, found 384.1945.

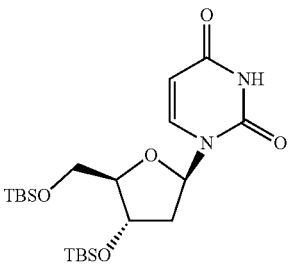

9

3',5'-O-TBDMS-2'-deoxyuridine (9). 2'-deoxyuridine (5.00 gm, 21.9 mmol), tert-butyldimethylsilyl chloride (9.91 gm, 65.8 mmol) and imidazole (8.93 gm, 131 mmol) are added to a dry round bottom flask and dissolved in 40.0 mL of DMF. The reaction is stirred at room temperature and monitored by TLC (10% methanol in DCM). After 18 h, the reaction is added to water and extracted with hexane. The crude product is purified with automated flash chromatography and product comes at 3-5% methanol in DCM. After evaporating the solvent, the product is collected as a white solid (9) (9.69 gm, 97.0% yield). $^1$H NMR (500 MHz, CDCl$_3$) δ 9.14 (s, 1H), 7.89 (d, J=8.1 Hz, 1H), 6.28 (t, J=6.2

Hz, 1H), 5.68 (d, J=8.1 Hz, 1H), 4.40 (dt, J=6.2, 4.0 Hz, 1H), 3.93-3.86 (m, 1H), 3.80-3.68 (m, 1H), 2.32 (ddd, J=13.3, 6.2, 4.3 Hz, 1H), 2.06 (dt, J=13.3, 6.2 Hz, 1H), 0.98-0.81 (m, 18H), 0.14--0.03 (m, 12H). $^{13}$C NMR (500 MHz, CDCl$_3$) δ 163.54, 150.39, 140.31, 102.28, 87.90, 85.27, 71.25, 62.52, 41.98, 26.00 (3C), 25.85 (3C), 18.48, 18.11, −4.47, −4.73, −5.37, −5.44. HR-ESI MS (m/z): [M+H]$^+$ calculated for C$_{21}$H$_{41}$N$_2$O$_5$Si$_2$ 457.2554, found 457.2575.

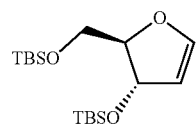

tert-butyl(((2R,3S)-3-((tert-butyldimethylsilyl)oxy)-2,3-dihydrofuran-2-yl)methoxy) dimethylsilane (10). (9) (2.00 gm, 4.39 mmol) and ammonium sulfate (289 mg, 2.19 mmol) are added to a round bottom flask, then hexamethyldisilazane (15.0 mL) is added and the reaction is refluxed for 4 h. The solvent is then evaporated under vacuum. The solid is dissolved in DCM; washed with water, saturated sodium bicarbonate and brine; and dried with sodium sulfate. The organic layer is evaporated then purified with automated flash chromatography and the product comes with 5% EtOAc in hexane (visualized on TLC by KMNO$_4$ dye). The solvent from purification is evaporated to give 393 mg (26.0% yield) of clear oily product (10). $^1$H NMR (500 MHz, CDCl$_3$) δ 6.46 (dd, J=2.8, 1.0 Hz, 1H), 5.00 (t, J=2.7 Hz, 1H), 4.86 (td, J=2.7, 1.0 Hz, 1H), 4.28 (td, J=6.0, 2.8 Hz, 1H), 3.69 (dd, J=10.7, 5.7 Hz, 1H), 3.50 (dd, J=10.7, 6.4 Hz, 1H), 0.89 (m, 18H), 0.13--0.00 (m, 12H). $^{13}$C NMR (500 MHz, CDCl$_3$) δ 149.09, 103.50, 89.13, 77.16, 76.09, 62.98, 26.06 (3C), 26.03 (3C), 18.55, 18.25, −4.10, −4.24, −5.19, −5.19.

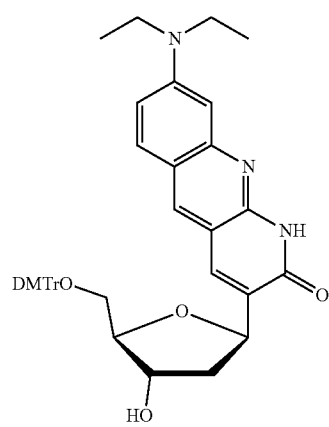

3-((2R,4R,5R)-5-((bis(4-methoxyphenyl)(phenyl)methoxy)methyl)-4-hydroxytetrahydrofuran-2-yl)-8-(diethylamino)benzo[b][1,8]naphthyridin-2(1H)-one (11). The nucleoside (7) (80 mg, 0.209 mmol) and 4,4'-dimethoxytrityl chloride (106 mg, 0.314 mmol) are dried under vacuum for 18 h then 2.5 mL of pyridine is added under nitrogen. The reaction mixture is stirred at room temperature for 1 h. The reaction is monitored by TLC (5% methanol in DCM) and quenched with methanol. The solvent is then evaporated, and automated flash chromatography is performed with the product eluting at 3-4% methanol in DCM (containing 1% triethylamine). The solvent from chromatography is evaporated to give 129 mg (90.0% yield) of yellow solid (11). $^1$H NMR (500 MHz, CDCl$_3$) δ 8.93 (s, 1H), 7.98 (d, J=1.3 Hz, 1H), 7.76 (s, 1H), 7.57 (d, J=9.2 Hz, 1H), 7.49 (d, J=7.7 Hz, 2H), 7.41-7.35 (m, 4H), 7.28 (t, J=7.8 Hz, 2H), 7.22 (t, J=7.3 Hz, 1H), 7.03 (dd, J=9.3, 2.5 Hz, 1H), 6.90 (d, J=2.4 Hz, 1H), 6.83 (d, J=8.3 Hz, 4H), 5.36 (t, J=7.5 Hz, 1H), 4.43 (s, 1H), 4.09 (d, J=4.2 Hz, 1H), 3.76 (s, 6H), 3.52 (q, J=7.1 Hz, 4H), 3.41-3.35 (m, 2H), 2.63-2.55 (m, 1H), 2.04 (dt, J=14.0, 6.9 Hz, 1H), 1.27 (t, J=7.0 Hz, 6H). $^{13}$C NMR (125 MHz, CDCl$_3$) δ 162.6, 158.7, 150.5, 148.5, 145.0, 136.2, 135.9, 133.8, 132.9, 130.3, 129.7, 128.4, 128.0, 127.0, 118.3, 114.9, 113.4, 111.8, 103.1, 85.4, 77.2, 75.2, 73.9, 64.2, 55.4, 44.9, 41.9, 12.9. HR-ESI MS (m/z): [M+H]$^+$ calculated for C$_{42}$H$_{44}$N$_3$O$_6$ 686.3230, found 686.3229.

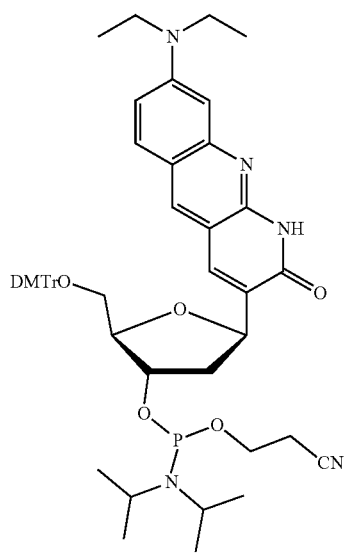

(2R,3R,5R)-2-((bis(4-methoxyphenyl) (phenyl)methoxy)methyl)-5-(8-(diethylamino)-2-oxo-1,2-dihydrobenzo[b][1,8]naphthyridin-3-yl)tetrahydrofuran-3-yl-2-cyanoethyldiisopropylphosphoramidite (12). The tritylated nucleoside (11) (100 mg, 0.146 mmol) is dissolved in 3 mL DCM then N,N-diisopropylethylamine (102 µL, 0.583 mmol) and 2-cyanoethyl-N,N-diisopropylchlorophosphoramidite (48.9 µL, 0.219 mmol) are added under nitrogen. The reaction mixture is stirred at room temperature for 3 h and monitored by TLC (5% methanol in DCM). The solvent is then evaporated, and automated flash chromatography is performed with the product eluting at 0-1% EtOAc in DCM (containing 1% triethylamine). The solvent from chromatography is evaporated, then the product is dissolved in minimal amount of DCM and recrystallized in cold hexane to give 60 mg (46.4% yield) of yellow solid (12). 1H NMR (500 MHz, CDCl$_3$) δ 8.84 (s, 1H), 8.07 (s, 0.5H), 8.02 (s, 0.5H), 7.72 (s, 0.5H), 7.65 (s, 0.5H), 7.59-7.54 (m, 1H), 7.51 (t, J=7.5 Hz, 2H), 7.39 (td, J=8.7, 2.2 Hz, 4H), 7.28 (d, J=7.6 Hz, 2H), 7.22 (d, J=7.6 Hz, 1H), 7.03 (d, J=9.4 Hz, 1H), 6.89 (s, 1H), 6.83 (t, J=7.6 Hz, 4H), 5.35 (t, J=7.4 Hz, 1H), 4.54 (d, J=30.6 Hz, 1H), 4.24-4.18 (m, 1H), 3.87-3.81 (m, 1H), 3.76 (s, 6H), 3.65-3.59 (m, 2H), 3.52 (q, J=7.1 Hz, 4H), 3.44-3.39 (m, 1H), 3.35-3.27 (m, 1H), 2.62 (d, J=6.3 Hz, 1H), 2.43 (t, J=6.5 Hz, 1H), 2.06-1.94 (m, 1H), 1.27 (t, J=7.0 Hz, 6H), 1.17 (m, 6H), 1.06 (d, J=6.8 Hz, 3H), 0.97 (d, J=6.6 Hz, 1H), 0.91-0.84 (m, 4H). 31P NMR (202 MHz, CDCl$_3$) δ 148.7, 147.9. HR-ESI MS (m/z): [M+H]⁺ calculated for C51H61N5O7P 886.4309, found 886.4310.

Example 2. Synthesis of Oligonucleotides

Oligonucleotides were generated by synthesizing ABN phosphoramidite using published methods and incorporated into DNA strands using solid-phase DNA synthesis performed by W. M. Keck Foundation (Yale School of Medicine). The HPLC-purified oligonucleotides were characterized by MALDI-TOF mass spectrometry and found to be consistent with calculated masses as shown in Table 3. Complementary DNA and unmodified DNA sequences were purchased from Integrated DNA Technologies, Inc. (San Diego, CA).

TABLE 3

ABN-modified oligonucleotides

| Oligo number | Sequence name | Sequence (5'-3') | Calculated mass [M + H] | Measured mass [M + H] |
|---|---|---|---|---|
| ODN1 | Hairpin | GCT TAG CAG GXT AGT GCT AAG C (SEQ ID NO: 1) | 6929.256 | 6933.297 |
| ODN4 | AXA | CGC AAX ATC G (SEQ ID NO: 2) | 3152.651 | 3152.006 |
| ODN7 | GXC | CGC AGX CTC G (SEQ ID NO: 3) | 3144.635 | 3143.611 |

TABLE 4

Complementary and unmodified oligonucleotides

| Oligo number | Sequence name | Sequence (5'-3') |
|---|---|---|
| ODN2 | HairpinA | GCT TAG CAC TAA CCT GCT AAG C (SEQ ID NO: 4) |
| ODN3 | HairpinG | GCT TAG CAC TAG CCT GCT AAG C (SEQ ID NO: 5) |
| ODN5 | TAT | CGA TAT TGC G (SEQ ID NO: 6) |
| ODN6 | TGT | CGA TGT TGC G (SEQ ID NO: 7) |
| ODN8 | GAC | CGA GAC TGC G (SEQ ID NO: 8) |
| ODN9 | GGC | CGA GGC TGC G (SEQ ID NO: 9) |
| ODN10 | HairpinT | GCT TAG CAG GTT AGT GCT AAG C (SEQ ID NO: 10) |
| ODN11 | ATA | CGC AAT ATC G (SEQ ID NO: 11) |
| ODN12 | GTC | CGC AGT CTC G (SEQ ID NO: 12) |
| ODN13 | HairpinC | GCT TAG CAG GCT AGT GCT AAG C (SEQ ID NO: 13) |
| ODN14 | ACA | CGC AAC ATC G (SEQ ID NO: 14) |
| ODN15 | GCC | CGC AGC CTC G (SEQ ID NO: 15) |

Example 3. Photophysical Measurements for 1P and 2P Single-Molecule Methods

Quantum yields measurements. Experiments were measured in a quartz sub-micro cuvette (10 mm path length) purchased from Starnacell Inc. Steady state emission scans were recorded using a PTI QuantaMaster QM-400 and absorbances were measured on a Shimadzu UV-1700 Pharmaspec spectrometer. Quantum yield measurements were performed the comparative method of Williams et. al. and measured in duplicate, at minimum. Coumarin 153 in ethanol was used as a reference standard for all photophysical measurements. All measurements were taken with an absorbance range of 0.01-0.1. Subsequent dilutions were performed stepwise in order to obtain a minimum of six absorbance and emission spectra for quantum yield determinations.

Sample and slide preparation for IP method. ABN (10 mM, DMSO) was diluted into filtered (0.2 μm syringe filter, Whatman, 6780-1302) PBS (pH 7.4) to a working concentration of 100 nM. Borosilicate glass coverslips (VWR Int, 22×22 mm) were cleaned for 1 hour using an argon plasma (PDC-002, Harrick Plasma). Frame-Seal slide chambers (9×9 mm², Biorad, Hercules, CA) were affixed to the glass and the slides washed three times with filtered PBS (3×50 μL). The working solution of ABN (100 nM, 50 μL) was added to the slide and left for 3-minutes allowing for some of the ABN molecules to adsorb to the plasma-cleaned glass surface. The excess solution containing unbound ABN was removed, and the slide washed once with filtered PBS (1×50 μL) to yield spatially isolated single dyes on the glass surface.

Single-molecule imaging. Single-molecule fluorescence imaging of ABN was performed on a bespoke total internal reflection fluorescence microscope using a 488 nm continuous wavelength diode laser (iBeamSMART, Toptica, 200.46 Wcm⁻²). The beam was circularly polarized using a wavelength specific quarter-wave plate and then expanded, collimated and aligned parallel to the optical axis at the edge of an objective lens (100× Plan Apo TIRF, NA 1.49 oil-immersion, Nikon Corporation) mounted on an inverted optical microscope (Ti2-Eclipse, Nikon Corporation). Fluorescence emission was collected by the same objective lens and separated from excitation light using a dichroic mirror (Di01-R405/488/561/635, Semrock) and passed through appropriate emission filters (BLP01-488R-25, FF01-520/44-25, Semrock). The fluorescence was then expanded (1.5×) and focused onto an electron-multiplying charge-coupled device (EMCCD, Evolve 512 Delta, Photometrics) with an electron multiplication gain of 250 ADU/photon operating in frame transfer mode. The effective pixel size was 107 nm. The instrument was automated using the open-source software micro-manager (v. 1.4) and the data displayed using the ImageJ software (v. 1.52d). Movies of single ABN emitters were collected for 150 frames at a rate of 10 fps.

Data analysis. A custom ImageJ macro was used to determine the total number of photons detected from single ABN emitters. The frames from single-molecule movies were summed and the pixel of peak intensity from each molecule was determined using the inbuilt 'Find Maxima' function (prominence threshold=20,000). The single emitters were selected from a 6×6 region surrounding the pixel of peak intensity and the total integrated intensity of the region was measured. 6×6 pixel regions surrounding the segmented emitters were used to determine the local background integrated intensity. The background intensity was then subtracted from the total intensity of the peak to yield the total integrated signal above background. The intensity per ABN emitter was converted from counts to photons detected by dividing the integrated signal above background by the total gain of the EMCCD (35.7 ADU/photon).

Sample preparation for 2P method. All experiments were done with a solution of approximately 100 nM of ABN in TRIS buffer (20 mM TRIS base) at a pH of 7.5. The molecules were initially dissolved in DMSO (at a concentration of 100 µM) and subsequently diluted in buffer. The TRIS buffer was prepared with ultrapure water (Direct Q3, Merck Millipore), TRIS-base (20 mM, Trizma base, BioUltra, Sigma-Aldrich) and 150 mM NaCl (analytical reagent grade, Fluka). The pH was adjusted to 7.5 with a HCl solution (Sigma-Aldrich). Prior to sample preparation, the buffer was filtered with activated charcoal (Darco, Fluca) and through a 0.2 µm filter (Milex, Merck).

Two photon microscope. The two-photon microscope is a homebuilt pulse-shaper assisted setup with a ultra-broadband Ti:Sa laser as light source, recently described (R. S. Fisher, et al., Phys. Chem. Chem. Phys., 20, 28487 (2018)). The excitation source was a broadband Ti: Sapphire laser with a repetition rate of 80 MHz and a spectrum centered on 800 nm with a FWHM of 135 nm (Vitara UBB, Coherent). The compressed pulses from the oscillator had a duration of 15 fs. To compensate for dispersion in the objective the pulses were compressed using the MIIPS method with a pulse shaper (Biophotonics, MIIPS-Box 640) (Lozovoy, V. V., et al. Opt. Lett. 29, 775(2004)). The beam was subsequently focused onto the sample by a 60× water-immersion objective (UPlanSApo, Olympus). The pulses at the sample had a duration of 8 fs. The sample was placed on a cover slip (Menzel Glaser, Thermo Scientific) and the solution temperature was controlled (22±1° C.) with an incubator (Live Cell Instrument, CU-501). Sample fluorescence was collected by the same objective and transmitted through a dichroic mirror (Chroma 675dcspxr) and a short pass filter (Semrock FF01-650/SP), split by a polarising beamsplitter cube and detected by two avalanche photodiodes (MPD PDM 50c and 1MPD $PD-050-CTB). The signal was subsequently detected by a hardware correlator (ALV-7002, ALV GmbH).

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula IA:

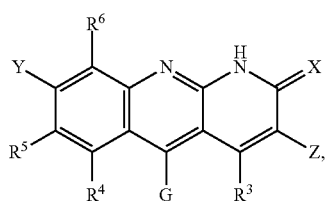

(IA)

or a salt thereof;

wherein

X is O, S, or $NR^a$, wherein $R^a$ is H or $—(C_1-C_{12})$alkyl;

Y is $NR^bR^c$, $OR^d$, $SR^e$, or

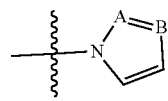

wherein A and B are each independently O, N, or S;

G is H, halo, or $—(C_1-C_{12})$alkyl;

$R^b$, $R^c$ $R^d$, and $R^e$ are each independently H or $—(C_1-C_{12})$alkyl;

R³, R⁴, R⁵ and R⁶ are each independently H, halo, OH, SH, NH₂, or —(C₁-C₁₂)alkyl; and Z is a monosaccharide or peptide;

wherein each —(C₁-C₁₂)alkyl moiety is unbranched or branched, saturated or partially unsaturated, and substituted optionally with one or more halo, OH or NH₂.

2. The compound of claim 1 wherein X is O.

3. The compound of claim 1 wherein Y is NR$^b$R$^c$.

4. The compound of claim 1 wherein R³, R⁴, R⁵ and R⁶ are each independently H, F, or CF₃.

5. The compound of claim 1 wherein Z is a furanose, ribose, or deoxyribose or deoxypyranose.

6. The compound of claim 1 wherein Z is 2-hydroxymethyl-3-hydroxytetrahydrofuran-5-yl.

7. The compound of claim 1 wherein the compound of Formula IA is a compound of Formula II:

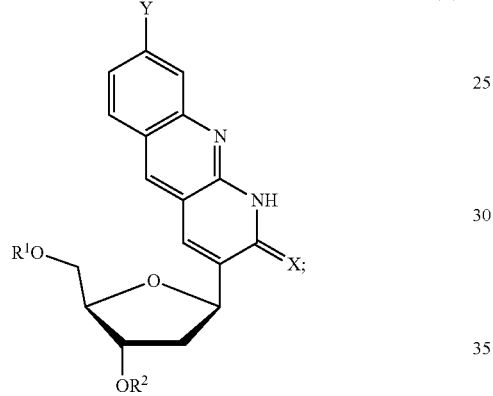

(II)

wherein R¹ and R² are each independently H, —(C₁-C₁₂) alkyl, triphosphate, a phosphoramidite, or protecting group.

8. The compound of claim 7 wherein X is O and Y is N(CH₂CH₃)₂.

9. The compound of claim 7 wherein R¹ and R² are each independently H, 4,4'-dimethoxytrityl (DMTr), or (2-cyanoethyl)-N,N-diisopropylphosphoramidityl.

10. The compound of claim 1 wherein the compound of Formula IA is 7', 11, 12, or ABN:

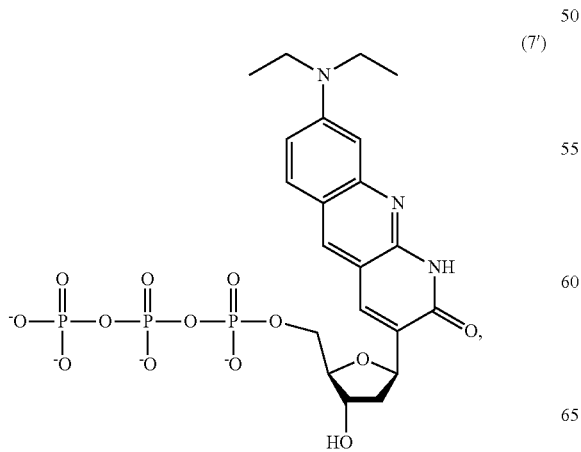

(7')

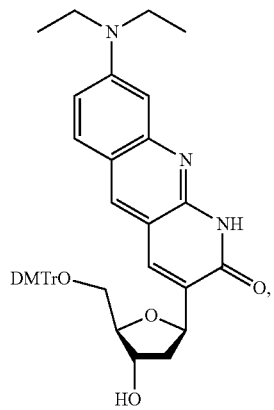

(11)

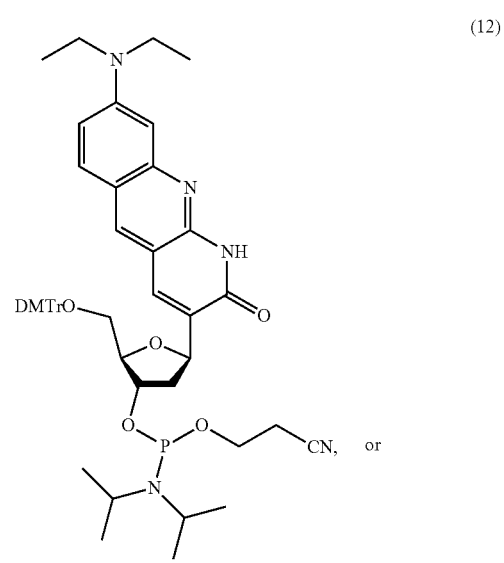

(12) or

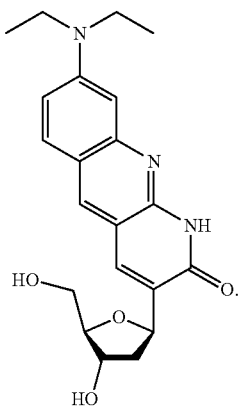

(ABN)

11. A method for imaging comprising:

a) incorporating into an oligonucleotide a compound of Formula IA:

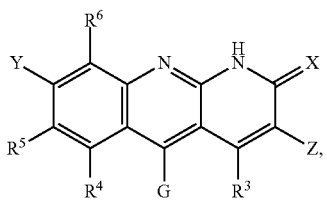

(IA)

or a salt thereof;
wherein
X is O, S, or NR$^a$, wherein R$^a$ is H or —(C$_1$-C$_{12}$)alkyl;
Y is NR$^b$R$^c$, OR$^d$, SR$^e$, or

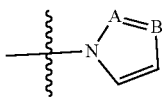

wherein A and B are each independently O, N, or S;
G is H, halo, or —(C$_1$-C$_{12}$)alkyl;
R$^b$, R$^c$ R$^d$, and R$^e$ are each independently H or —(C$_1$-C$_{12}$)alkyl;
R$^3$, R$^4$, R$^5$ and R$^6$ are each independently H, halo, OH, SH, NH$_2$, or —(C$_1$-C$_{12}$)alkyl; and
Z is a monosaccharide;
wherein each —(C$_1$-C$_{12}$)alkyl moiety is unbranched or branched, saturated or partially unsaturated, and substituted optionally with one or more halo, OH or NH$_2$;
b) exciting the compound at a suitable wavelength to form a fluorescing compound, wherein one or more photons excite a single molecule of the compound; and
c) counting the number of photons emitted by the fluorescing compound as a function of time;
wherein the base-paired compound is thereby imaged.

12. The method of claim 11 wherein the compound of Formula IA is 8-(diethylamino)-3-((2R,4S,5R)-4-hydroxy-5-(hydroxymethyl)tetrahydrofuran-2-yl)benzo[b][1,8]naphthyridin-2(1H)-one (ABN).

13. The method of claim 11 wherein the monosaccharide group (Z) of the compound is covalently bound to one or more nucleic acids of the oligonucleotide via one or more phosphodiester groups.

14. The method of claim 11 further comprising scavenging oxygen in a mixture comprising an oxygen scavenger and the incorporated compound.

15. The method of claim 11 comprising contacting a compound of Formula IA and the oligonucleotide under suitable conditions for oligonucleotide synthesis wherein the synthesis proceeds in the 3'- to 5'-direction and the compound is covalently bound to the oligonucleotide.

16. The method of claim 11 wherein the compound of Formula IA is a compound of Formula II:

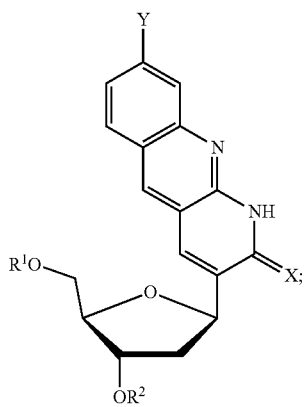

(II)

wherein R$^1$ and R$^2$ are each independently H, —(C$_1$-C$_{12}$) alkyl, triphosphate, a phosphoramidite, or protecting group.

17. The method of claim 11 wherein the compound is (2R,3R,5R)-2-((bis(4-methoxyphenyl)(phenyl)methoxy) methyl)-5-(8-(diethylamino)-2-oxo-1,2-dihydrobenzo[b][1,8]naphthyridin-3-yl)tetrahydrofuran-3-yl (2-cyanoethyl) diisopropylphosphoramidite (12).

18. The method of claim 11 wherein the suitable wavelength to excite the base-paired compound is about 415 nanometers to about 445 nanometers and/or the fluorescing compound has an emission wavelength of about 470 nanometers to about 545 nanometers.

19. The method of claim 11 wherein the based-paired compound is imaged by fluorescence correlation spectroscopy, fluorescence spectroscopy, single-molecule fluorescence spectroscopy, Förster resonance energy transfer (FRET), or single-molecule FRET.

20. The method of claim 11 wherein a single molecule of the fluorescing compound emits a sufficient number of photons to be imaged by fluorescence correlation microscopy.

* * * * *

SEQUENCE LISTING

```
<160> NUMBER OF SEQ ID NOS: 18

<210> SEQ ID NO 1
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: n is 8-(diethylamino)-3-((2R,4R,5R)-4-hydroxy-
      5-(hydroxymethyl)tetrahydrofuran-2-yl)benzo[b][1,8]naphthyridin-
      2(10H)-one

<400> SEQUENCE: 1
gcttagcagg ntagtgctaa gc                                              22

<210> SEQ ID NO 2
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is 8-(diethylamino)-3-((2R,4R,5R)-4-hydroxy-
      5-(hydroxymethyl)tetrahydrofuran-2-yl)benzo[b][1,8]naphthyridin-
```

2(10H)-one

<400> SEQUENCE: 2 cgcaanatcg                                                            10

<210> SEQ ID NO 3
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is 8-(diethylamino)-3-((2R,4R,5R)-4-hydroxy-
    5-(hydroxymethyl)tetrahydrofuran-2-yl)benzo[b][1,8]naphthyridin-
    2(10H)-one

<400> SEQUENCE: 3 cgcagnctcg                                                            10

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
gcttagcact aacctgctaa gc                                              22

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
gcttagcact agcctgctaa gc                                              22

<210> SEQ ID NO 6
<211> LENGTH: 10
<212> TYPE: DNA
<213> ORGANISM: Artificial Sequence
<220> FEATURE:
<223> OTHER INFORMATION: Synthetic

<400> SEQUENCE: 6
cgatattgcg                                                            10

<210> SEQ ID NO 7
<211> LENGTH: 10
<212> TYPE: DNA
<213> ORGANISM: Artificial Sequence
<220> FEATURE:
<223> OTHER INFORMATION: Synthetic

<400> SEQUENCE: 7
cgatgttgcg                                                            10

<210> SEQ ID NO 8
<211> LENGTH: 10
<212> TYPE: DNA
<213> ORGANISM: Artificial Sequence
<220> FEATURE:
<223> OTHER INFORMATION: Synthetic

```
<400> SEQUENCE: 8
cgagactgcg                                                              10

<210> SEQ ID NO 9
<211> LENGTH: 10
<212> TYPE: DNA
<213> ORGANISM: Artificial Sequence
<220> FEATURE:
<223> OTHER INFORMATION: Synthetic

<400> SEQUENCE: 9
cgaggctgcg                                                              10

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
gcttagcagg ttagtgctaa gc                                                22

<210> SEQ ID NO 11
<211> LENGTH: 10
<212> TYPE: DNA
<213> ORGANISM: Artificial Sequence
<220> FEATURE:
<223> OTHER INFORMATION: Synthetic

<400> SEQUENCE: 11
cgcaatatcg                                                              10

<210> SEQ ID NO 12
<211> LENGTH: 10
<212> TYPE: DNA
<213> ORGANISM: Artificial Sequence
<220> FEATURE:
<223> OTHER INFORMATION: Synthetic

<400> SEQUENCE: 12
cgcagtctcg                                                              10

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
gcttagcagg ctagtgctaa gc                                                22

<210> SEQ ID NO 14
<211> LENGTH: 10
<212> TYPE: DNA
<213> ORGANISM: Artificial Sequence
<220> FEATURE:
<223> OTHER INFORMATION: Synthetic

<400> SEQUENCE: 14
cgcaacatcg                                                              10

<210> SEQ ID NO 15
```

```
<211> LENGTH: 10
<212> TYPE: DNA
<213> ORGANISM: Artificial Sequence
<220> FEATURE:
<223> OTHER INFORMATION: Synthetic

<400> SEQUENCE: 15
cgcagcctcg                                                              10

<210> SEQ ID NO 16
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: r is a or g

<400> SEQUENCE: 16
gcttagcact arcctgctaa gc                                                22

<210> SEQ ID NO 17
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: r is a or g

<400> SEQUENCE: 17 cgatrttgcg                                                              10

<210> SEQ ID NO 18
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: r is a or g

<400> SEQUENCE: 18 cgagrctgcg                                                              10
```